United States Patent
Lassner et al.

(10) Patent No.: US 9,610,301 B2
(45) Date of Patent: Apr. 4, 2017

(54) POWDERED PROTEIN COMPOSITIONS AND METHODS OF MAKING SAME

(75) Inventors: Peter K. Lassner, Forcheim (DE); Michael Adler, Freiburg (DE); Geoffrey Lee, Erlangen (DE); Hans-Juergen Krause, Gruenstadt (DE); Michael Siedler, Munich (DE)

(73) Assignee: ABBVIE DEUTSCHLAND GMBH & CO KG (DE)

( * ) Notice: Subject to any disclaimer, the term of this patent is extended or adjusted under 35 U.S.C. 154(b) by 344 days.

(21) Appl. No.: 12/354,665

(22) Filed: Jan. 15, 2009

(65) Prior Publication Data

US 2009/0226530 A1 Sep. 10, 2009

Related U.S. Application Data

(60) Provisional application No. 61/021,298, filed on Jan. 15, 2008.

(51) Int. Cl.
| | |
|---|---|
| *A61K 39/395* | (2006.01) |
| *A61K 31/70* | (2006.01) |
| *A61K 9/16* | (2006.01) |
| *A61K 31/715* | (2006.01) |
| *A61K 47/26* | (2006.01) |
| *C07K 16/24* | (2006.01) |

(52) U.S. Cl.
CPC ............ *A61K 31/70* (2013.01); *A61K 9/1605* (2013.01); *A61K 31/715* (2013.01); *A61K 39/39591* (2013.01); *A61K 47/26* (2013.01); *C07K 16/241* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,231,024 A | 7/1993 | Moeller et al. | |
| 5,654,407 A | 8/1997 | Boyle et al. | |
| 5,656,272 A | 8/1997 | Le et al. | |
| 5,795,967 A | 8/1998 | Aggarwal et al. | |
| 5,859,205 A | 1/1999 | Adair et al. | |
| 5,877,293 A | 3/1999 | Adair et al. | |
| 5,929,212 A | 7/1999 | Jolliffe et al. | |
| 5,994,510 A | 11/1999 | Adair et al. | |
| 6,090,382 A | 7/2000 | Salfeld et al. | |
| 6,258,562 B1 | 7/2001 | Salfeld et al. | |
| 6,270,766 B1 | 8/2001 | Feldman et al. | |
| 6,284,282 B1 | 9/2001 | Maa et al. | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 6,593,458 B1 | 7/2003 | Rathjen et al. | |
| 6,685,940 B2 * | 2/2004 | Andya et al. ............ 424/133.1 |
| 6,914,128 B1 | 7/2005 | Salfeld et al. | |
| 7,070,775 B2 | 7/2006 | Le et al. | |
| 7,192,584 B2 | 3/2007 | Le et al. | |
| 7,223,394 B2 | 5/2007 | Salfeld et al. | |
| 7,250,165 B2 | 7/2007 | Heavner et al. | |
| 7,276,239 B2 | 10/2007 | Le et al. | |
| 7,521,206 B2 | 4/2009 | Heavner et al. | |
| 7,541,031 B2 | 6/2009 | Salfeld et al. | |
| 7,588,761 B2 | 9/2009 | Salfeld et al. | |
| 7,863,426 B2 | 1/2011 | Wan et al. | |
| 2003/0012786 A1 | 1/2003 | Teoh et al. | |
| 2003/0049725 A1 | 3/2003 | Heavner et al. | |
| 2003/0064105 A1 | 4/2003 | Kim et al. | |
| 2003/0148955 A1* | 8/2003 | Pluenneke .................... 514/12 |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2003/0235585 A1 | 12/2003 | Fischkoff et al. | |
| 2004/0009172 A1 | 1/2004 | Fischkoff et al. | |
| 2004/0033228 A1 | 2/2004 | Krause et al. | |
| 2004/0120952 A1 | 6/2004 | Knight et al. | |
| 2004/0126372 A1 | 7/2004 | Banerjee et al. | |
| 2004/0126373 A1 | 7/2004 | Banerjee et al. | |
| 2004/0131614 A1 | 7/2004 | Banerjee et al. | |
| 2004/0136989 A1 | 7/2004 | Banerjee et al. | |
| 2004/0136990 A1 | 7/2004 | Banerjee et al. | |
| 2004/0136991 A1 | 7/2004 | Banerjee et al. | |
| 2004/0151722 A1 | 8/2004 | Banerjee et al. | |

(Continued)

FOREIGN PATENT DOCUMENTS

| | | |
|---|---|---|
| DE | 10 2006 030164 | 1/2008 |
| EP | 351 789 A2 | 1/1990 |

(Continued)

OTHER PUBLICATIONS

Abraham et al., "Efficacy and Safety of Monoclonal Antibody to Human Tumor Necrosis Factor α in Patients with Sepsis Syndrome," *JAMA*, vol. 273(12):934-941 (1995).

Barbuto et al., "Production of Neutralizing Antibodies to Tumor Necrosis Factor by Human Tumor-Infiltrating B Lymphocytes" *Proc. Am. Assoc. Cancer Res,.* 34:487, Abstr. 2904 (1993).

Bendtzen et al., "Auto-antibodies to IL-1α and TNFα in Normal Individuals and in Infectious and Immunoinflammatory Disorders" *The Physiological and Pathological Effects of Cytokines*, 447-52 (1990).

Boekstegers et al., "Repeated administration of a F(ab')2 fragment of an anti-tumor recrosis factor alpha monoclonal antibody in patients with severe sepsis: effects on the cardiovascular system and cytokine levels," *Shock*, vol. 1(4):237-245 (1994) (abstract from Pub Med).

(Continued)

*Primary Examiner* — Yunsoo Kim

(74) *Attorney, Agent, or Firm* — McCarter & English, LLP; Cristin H. Cowles; Deborah L. Nagle

(57) ABSTRACT

A method for preparing a protein or peptide powder is provided that includes spray drying a solution including more than, e.g., about 50 mg/mL of a protein or peptide (e.g., an antibody or antigen binding portion thereof), and at least one excipient. Also provided are stable powdered compositions including a protein and an excipient having less than, e.g., about 6% residual moisture.

6 Claims, 7 Drawing Sheets

(56) References Cited

U.S. PATENT DOCUMENTS

| | | |
|---|---|---|
| 2004/0166111 A1 | 8/2004 | Kaymakcalan et al. |
| 2004/0185091 A1* | 9/2004 | Truong-Le et al. .......... 424/450 |
| 2004/0191243 A1 | 9/2004 | Chen et al. |
| 2004/0219142 A1 | 11/2004 | Banerjee et al. |
| 2005/0123541 A1 | 6/2005 | Heavner et al. |
| 2005/0147610 A1 | 7/2005 | Ghayur et al. |
| 2005/0249735 A1 | 11/2005 | Le et al. |
| 2005/0250704 A1 | 11/2005 | Bassarab et al. |
| 2006/0009385 A1 | 1/2006 | Hoffman et al. |
| 2006/0018907 A1 | 1/2006 | Le et al. |
| 2006/0083741 A1 | 4/2006 | Hoffman et al. |
| 2006/0127460 A1* | 6/2006 | Uchida et al. ................ 424/445 |
| 2006/0153846 A1 | 7/2006 | Krause et al. |
| 2006/0246073 A1 | 11/2006 | Knight et al. |
| 2007/0041905 A1 | 2/2007 | Hoffman et al. |
| 2007/0059363 A1 | 3/2007 | Lee et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2007/0298116 A1 | 12/2007 | Bechtold-Peters et al. |
| 2008/0025976 A1 | 1/2008 | Le et al. |
| 2008/0089849 A1 | 4/2008 | Schultz-Fademrecht et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong et al. |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |

FOREIGN PATENT DOCUMENTS

| | | |
|---|---|---|
| EP | 366 043 A1 | 5/1990 |
| EP | 492 448 A1 | 7/1992 |
| EP | 186 833 B1 | 8/1992 |
| EP | 0 260 610 | 9/1993 |
| EP | 614 984 A2 | 9/1994 |
| EP | 212 489 B1 | 11/1994 |
| EP | 101 681 B1 | 12/1994 |
| EP | 659 766 A1 | 6/1995 |
| GB | 2 279 077 | 12/1994 |
| WO | WO 91/02078 | 2/1991 |
| WO | WO 92/11383 | 7/1992 |
| WO | WO 92/16553 | 10/1992 |
| WO | WO 93/06213 | 4/1993 |
| WO | WO 94/29347 | 12/1994 |
| WO | WO 95/23813 A1 | 9/1995 |
| WO | WO-96/18647 A1 | 6/1996 |
| WO | WO 97/29131 | 8/1997 |
| WO | WO-99/13900 A1 | 3/1999 |
| WO | WO 02/11695 | 2/2002 |
| WO | WO 02/12502 | 2/2002 |
| WO | WO 2004/060343 | 7/2004 |
| WO | WO-2004058156 A2 | 7/2004 |
| WO | WO 2005/102284 | 11/2005 |
| WO | WO 2007/005608 | 1/2007 |
| WO | WO 2008/127271 | 10/2008 |

OTHER PUBLICATIONS

Boyle et al., "A Novel Monoclonal Human IgM Autoantibody which Binds Recombinant Human and Mouse Tumor Necrosis Factor-α" *Cell. Immunol.*, 152:556-68 (1993).

Boyle et al., "The B5 Monoclonal Human Autoantibody Binds to Cell Surface TNF.alpha. on Human Lymphoid Cells and Cell Lines and Appears to Recognize a Novel Epitope", *Cell. Immunol.*, vol. 152, pp. 569-581, (1993).

Brekke et al., "Therapeutic antibodies for human diseases at the dawn of the twenty-first century," *Nature Reviews/Drug Discovery*, vol. 2:52-62 (2003).

Chow et al.,"Effect of monoclonal antibody on human tumor necrosis factor (TNF MAb) on TNFα, IL-1β, and IL-6 levels in patients with sepsis syndrome" *Clinical Research*, vol. 42, No. 2 p. 299A (1994).

Cohen et al.,"Intersept: An international, multicenter, placebo-controlled trial of monoclonal anitbody to human tumor necrosis factor-α in patients with sepsis," *Crit Care Med*, vol. 24(9):1431-1440 (1996).

Cox et al., "A directory of human germ-line $V_K$ segments reveals a strong bias in their usage" *Eur. J. Immunol.*, 24(2):827-36 (1994).

Department of Surgery, University of Toronto Annual Report, Jul. 1, 1998-Jun. 30, 1999—found online at http://www.surg.med.utoronto.ca/AnnRep/AR98_99/index.html.

Doring et al., "Identification and Characterization of a TNFa Antagonist Derived from a Monoclonal Antibody," *Mol Immunol.*, 31(14): 1059-1067 (1994).

Elliot et al., "Treatment of rheumatoid arthritis with chimeric monoclonal antibodies to human tumor necrosis factor α" *Arthritis & Rheumatism*, 36(12):1681-90 (1993).

Feldman et al., "Anti-TNFα Therapy of Rheumatoid Arthritis: What Have We Learned?" *Annu. Rev. Immunol.*, vol. 19:163-196 (2001).

Figini et al., "In Vitro Assembly of Repertoires of Antibody Chains on the Surface of Phage by Renaturation," *J. Mol. Biol.*, vol. 239:68-78 (1994).

Fomsgaard et al., "Auto-antibodies to Tumour Necrosis Factor α in Healthy Humans and Patients with Inflammatory Diseases and Gram-Negative Bacterial Infections" *Scand. J. Immunol.*, 30:219-23 (1989).

Foote et al. "Antibody framework residues affecting the conformation of the hypervariable loops," *J Mol Biol* 224(2):487 (1992).

Griffiths et al., "Human anti-self antibodies with high specificity from phage display libraries" *The EMBO J.*, 12(2):725-34 (1993).

Hawkins et al., "Selection of Phage Antibodies by Binding Affinity Mimicking Affinity Maturation," *J. Mol. Biol.*, vol. 226:889-896 (1992).

Holler et al., "Modulation of acute graft-versus-host-disease after allogeneic bone marrow ransplantation by tumor necrosis factor alpha (TNF alpha) release in the course of pretransplant conditioning: role of conditioning regimens and prophylactic application of a monoclonal antibody neutralizing human TNF alpha (MAK 195F)," *Blood*, vol. 86(3):890-899 (1995) (abstract from Pub Med).

Hoogenboom et al., "Converting rodent into human antibodies by guided selection," *Antibody Engineering*, Oxford University Press, pp. 169-185 (1996).

Huse et al., "Generation of a large combinatorial library of the immunoglobulin repertoire in phage lambda" *Science*, 246:1275-81 (1989).

Jespers et al., "Guiding the Selection of Human Antibodies from Phage Display Repertoires to a Single Epitope of an Antigen," *Bio/Technology*, vol. 12:899-903 (1994).

Kempeni, "Update on D2E7: a fully human anti-tumor necrosis factor α monoclonal antibody," *Ann Rheum Dis*, vol. 59(Suppl. 1)144-145 (2000).

Lerner et al., "Antibodies without immunization" *Science*, 258:1313-14 (1992).

(56) References Cited

OTHER PUBLICATIONS

Leusch et al., "Failure to demonstrate TNFα-specific autoantibodies in human sera by ELISA and Western blot" *J. Immunol. Methods*, 139:145-47 (1991).
Lewis et al., "Use of alanine scanning mutagenesis to improve the affinity of an anti gp120 (HIV) antibody." *J. Cell. Biochem.*, 18D:215 (1994).
Low, thesis extract, Cambridge University (1996).
Low et al., "Mimicking Somatic Hypermutation: Affinity Maturation of Antibodies Displayed on Bacteriophage Using a Bacterial Mutator Strain," *J. Mol. Biol.*, vol. 260:359-368 (1996).
Marks et al., "By-Passing Immunization: Building High Affinity Human Antibodies By Chain Shuffling," *Biotechnology* 10:779-783 (1992).
Marks et al. "By-passing immunization: Human antibodies from V-gene libraries displayed on phage" *J. Mol. Biol.* 222:581-97 (1991).
Medynski, "Phage Display: All Dressed Up and Ready to Role," *Bio/Technology*, vol.12:1134-1136 (1994).
Möller et al., "Monoclonal antibodies to human tumor necrosis factor α: in vitro and vivo application" *Cytokine*, 2(3):162-69 (1990).
Nilsson, "Antibody engineering," *Current Opinion in Structural Biology*, vol. 5:450-456 (1995).
Osbourn et al., "From rodent reagents to human therapeutics using antibody guided selection," *Methods* 36(1):61 (2005).
Queen et al., "A humanized antibody that binds to the interleukin 2 receptor," *PNAS USA*, 86(24):10029 (1989).
Riechmann et al., "Phage display and selection of a site-directed randomized single-chain antibody Fv fragment for its affinity improvement," *Biochemistry*, vol. 32(34):8848-8855 (1993) (abstract from Pub Med).
Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study." 1996 Crit. Care. Med., vol. 24(5):733-742.
Santora et al., "Characterization of Noncovalent Complexes of Recombinant Human Monoclonal Antibody and Antigen Using Cation Exchange, Size Exclusion Chromatography, and BIA core," *Analytical Biochemistry*, vol. 299:119-129 (2001).
Thompson et al., "Affinity maturation of a high-affinity human monoclonal antibody against the third hypervariable loop of human immunodeficiency virus: use of phage display to improve affinity and broaden strain reactivity," *J. Mol. Biol.*, vol. 256(1):77-88 (1996) (abstract from Pub Med).
Tomlinson et al., "The Repertoire of Human Germline $V_H$ Sequences Reveals about Fifty Groups of $V_H$ Segments with Different Hypervariable Loops," *J. Mol. Biol.*, vol. 227:776-798 (1992).
Tomlinson et al., "The structural repertoire of the human $V_\kappa$ domain," *The EMBO Journal*, vol. 14(18):4628-4638 (1995).
Tracey et al., "Tumor Necrosis Factor: A Pleiotropic Cytokine and Therapeutic Target," *Annu. Rev. Med.*, vol. 45:491-503 (1994).
Van Der Poll et al., "Effect of postponed treatment with an anti-tumour necrosis factor (TNF) F(ab')2 fragment on endotoxin-induced cytokine and neutrophil responses in chimpanzees," *Clin Exp Immunol*, vol. 100:21-25 (1995).
Vaughan et al., "Human antibodies by design," *Nature Biotechnology*, vol. 16:535-539 (1998).
Ward et al., "Binding activities of a repertoire of single immunoglobulin variable domains secreted from *Escherichia coli*," *Nature*, vol. 341(6242):544-546 (1989).
Winter et al, "Humanized antibodies," *Immunology Today*, vol. 14(6):243-246 (1993).
Winter et al., "Making antibodies by phage display technology," *Annu. Rev. Immunol.*, vol. 12:433-455 (1994).
Zhao et al., "Recent U.S. Patents on Protein Drug Formulation: 2000-2007," *Recent Patents on Drug Delivery and Formulation*, 2(3):200-208(9) (2008).
Daugherty et al., "Formulation and delivery issues for monoclonal antibody therapeutics," *Advanced Drug Delivery Reviews*, 58:686-706 (2006).
Rader et al., "A phage display approach to rapid antibody humanization: Designed combinatorial V gene libraries," *Proc Natl Acad Sci USA*, vol. 95:8910-8915 (1998).
Dani et al., "High Concentration Formulation Feasibility of Human Immunoglubulin G for Subcutaneous Administration", Journal of Pharmaceutical Sciences, 2007, vol. 96, No. 6, pp. 1504-1517.

\* cited by examiner

POWDERED PROTEIN COMPOSITIONS AND METHODS OF MAKING SAME

RELATED APPLICATIONS

This application claims the benefit of priority to U.S. provisional patent application No. 61/021,298 filed 15 Jan. 2008, the contents each of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 23, 2013, is named SeqList and is 3,890 bytes in size.

BACKGROUND OF THE INVENTION

A basic principle of pharmaceutical protein formulations is that certain instabilities must be overcome. Degradation pathways of proteins can be separated into two distinct classes, involving chemical instability and physical instability. Chemical instabilities lead to the modification of the protein through bond formation or cleavage. Examples of chemical instability problems include deamidation, racemization, hydrolysis, oxidation, beta elimination and disulfide exchange. Physical instabilities, on the other hand, do not lead to covalent changes in proteins. Rather, they involve changes in the higher order structure (secondary and above) of proteins. These include denaturation, adsorption to surfaces, aggregation and precipitation. Manning et al., *Pharm. Res.* 6, 903 (1989).

After the discovery of the DNA-structure by Watson and Crick (1953) and the subsequent completion of the human genome sequencing project, the interest in protein chemistry grew very fast. The relationship between genes and their protein products in disease, tissues or development was of particular interest. *Next generation pharmaceutical*, Issue 6 (GDS publishing Ltd., 2006). Over the intervening decades, the number of protein-based pharmaceuticals increased very fast. Today, certain proteins or peptides can be isolated or synthesized, modified and delivered for easing or healing certain disorders and diseases. The main application pathway for protein-based pharmaceuticals is still the intravenous injection of liquid formulations, but other pathways have also been tested and used.

Many efforts have been made to transfer protein solutions into solid forms. Powdered compositions offer many advantages, e.g., larger amounts of protein can be stored or transported by involving much less space and weight, and energy consumption is lower than that required for cooling the liquid formulations during storage and shipping. Powdered compositions also facilitate new routes of delivery, such as inhalation (Tzannis et al., International Publication No. WO 2005067898), or needle-free injection (Burkoth, *The Drug Delivery Companies Report* 76-78 (2001)). Several methods have been employed for producing powders from aqueous protein solutions, among them spray drying, spray-freeze drying, freeze drying, or precipitation from supercritical fluids or (partially) organic solutions. Winters et al., *Journal of Pharm. Sci.* 85(6): 586-594 (1996). In contrast to freeze drying, which is very expensive and time-consuming, spray drying is an effective, efficient means of producing protein-loaded solids that provide opportunities for the development of new delivery forms for biopharmaceuticals, such as inhalation. Maa et al., *Pharm. Res.* 16(2): 249-254 (1999).

Spray drying a pure protein solution runs the risk of causing partial inactivation, which automatically leads to a lower quality pharmaceutical. Inactivation can, e.g., be caused by process related physical stress due to high temperatures, shear stress and the large phase interface (liquid/gas), such as denaturation or aggregation, or by chemical reactions, e.g., hydrolysis or oxidation.

SUMMARY OF THE INVENTION

The present invention relates to methods for spray drying protein formulations that comprise a protein and an excipient. Specifically, the methods and compositions of the invention are based on a spray drying process wherein a solution containing the protein of interest and an excipient is spray dried.

The formulation of the invention has many advantages over standard solution and freeze dried formulations. In particular, the spray drying methods of the invention minimize process related degradation and increase protein stability at ambient temperatures (e.g., as compared to freeze dried compositions). Furthermore, the spray dried formulations are also easier to transport, and are useful for manufacturing high concentration formulations, improving the bioavailability of the protein, and development of local release (e.g., pulmonary delivery) and sustained release (e.g., liposomal and (poly(D,L-lactide-co-glycolide)) PLGA-coated microsphere) formulations.

The methods and compositions of the invention may be used to provide a stable powdered composition or formulation including any protein of interest and an excipient. In one aspect, the methods and compositions of the invention are used for antibodies and fragments thereof, including those used for in vivo and in vitro purposes. In a further embodiment, the antibody fragment is an immunoglobulin G (IgG) fragment.

Furthermore, the multiple step purification and concentration processes that are necessary to prepare proteins and peptide formulations often introduce variability in compositions, such that the precise composition of a formulation may vary from lot to lot. Federal regulations require that drug compositions be highly consistent in their formulations regardless of the location of manufacture or lot number. Methods of the invention can be used to create powdered formulations of proteins to which excipients are added in precise amounts, allowing for the creation of protein formulations with precise concentrations of excipients.

In one aspect, the invention provides a method for preparing a protein or peptide powder that includes spray drying a solution comprising more than about 50 mg/mL of a protein or peptide, and at least one excipient, such that a protein or peptide powder is prepared. In some embodiments, the solution comprises more than about 100 mg/mL of the protein or peptide. The protein may also be a dual variable binding domain (DVD) binding protein.

In some embodiments, the method includes preparing an antibody powder, which includes spray drying a solution comprising more than about 50 mg/mL of an antibody, or antigen binding portion thereof, and at least one excipient, such that an antibody powder is prepared. In some embodiments, the solution comprises more than about 100 mg/mL of the antibody, or antigen binding portion thereof. The antibody, or antigen binding portion thereof, can be an immunoglobulin G (IgG), e.g., MAK 195F, Adalimumab, ABT-325, ABT-308 or ABT-147. In some embodiments, the powder is stable at ambient temperatures and humidity for at least three months and/or stable at 40° C. for at least three months.

The excipient can include, e.g., trehalose, sucrose, sorbitol, polyethylene glycol, at least one amino acid, histidine, alanine, arginine, glycine, or a mixture thereof. In some embodiments, the solution includes an excipient:protein ratio of between about 0.27:1.0 and about 2.8:1.0, between about 0.27:1.0 and about 1.4:1.0, between about 0.27:1.0 and about 0.7:1.0, or a ratio of about 0.7:1.0. In some embodiments, the solution comprises between about 20 and about 30 mM excipient, or about 25 mM excipient.

In some embodiments, the method includes spray drying with an inlet air temperature ($T_{in}$) between about 100° C. and about 180° C., and an outlet air temperature ($T_{out}$) between about 60° C. and about 110° C. In certain embodiments, the method includes spray drying with a $T_{in}$ of about 130° C. and a $T_{out}$ of about 80° C. The method can include, e.g., atomizing the solution to form solution droplets, drying the droplets with a gas to form a powder, and recovering the powder from the gas. The method can include atomizing the solution with a pressure nozzle atomizer and/or separating and recovering the antibody powder from the gas with a cyclone.

The method can also include embedding the antibody powder in a pharmaceutically acceptable carrier. The pharmaceutically acceptable carrier can be acceptable for parental, oral, enteral, and/or topical administration. The pharmaceutically acceptable carrier can include a liquid such as water.

In another aspect, the invention is directed to a pharmaceutical preparation that includes an effective amount of an antibody, or an antigen binding portion thereof, prepared according to any of the methods described herein. In yet another aspect, the invention is directed to a pharmaceutical preparation that includes an effective amount of a protein or peptide, prepared according to any of the methods described herein.

In yet another aspect, the invention provides a stable powdered composition including a protein or peptide, and an excipient, wherein the composition includes less than about 6% residual moisture, in some embodiments, less than about 4% or 3% residual moisture. The protein or peptide can include an antibody, or an antigen binding portion thereof, such as an IgG antibody, or antigen binding portion thereof, such as e.g., MAK 195F, Adalimumab, ABT-325, ABT-308 or ABT-147. The protein may also be a dual variable binding domain (DVD) binding protein.

In some embodiments, the powdered composition is stable at ambient temperatures and humidity for at least three months and/or at about 40° C. for at least three months. In some embodiments, the protein or peptide, or antibody, or antigen binding portion thereof, retains its biological activity.

The excipient can include trehalose, sucrose, sorbitol, polyethylene glycol, at least one amino acid, histidine, alanine, arginine, glycine, or a mixture thereof. The composition can have a mass ratio of excipient (e.g., trehalose and/or sucrose) to antibody, or antigen binding portion thereof, of about 0.27:1.0 to about 2.8:1.0, about 0.27:1.0 to about 1.4:1.0, about 0.27:1.0 to about 0.7:1.0, or about 0.7:1. The composition can have a mass ratio of excipient (e.g., sorbitol) to antibody, or antigen binding portion thereof, of about 0.27:1.0 to about 2.8:1.0, about 0.27:1.0 to about 1.4:1.0, about 0.27:1.0 to about 0.7:1.0, of about 0.7:1, or about 0.35:1.

In yet another aspect, the invention provides a method of manufacturing a pharmaceutical composition that includes mixing an effective amount of a stable powdered composition of the invention with a pharmaceutically acceptable carrier, e.g., a liquid such as water. In some embodiments, the pharmaceutical composition is adapted for parental, oral, enteral, or topical administration. The method can further include processing the stable powdered composition at a temperature significantly above ambient temperature (e.g., melt extruding) without significantly affecting the stability of the powdered composition.

In certain embodiments, the method includes coating the powdered composition, e.g., with a polymer such as PLGA to form a sustained release or delayed release pharmaceutical composition. Additionally or alternatively, the method can include coating with an enteric coating. In some embodiments, the activity of the protein, peptide, antibody, or antigen binding portion thereof, is protected by the excipient against precipitation, denaturation or oxidation by organic solvents, e.g., PEG 400, ethanol, DMSO, NMP, or glacial acetic acid.

Currently, nearly all companies use frozen bulk drug compositions and face problems such as reproducibility of the freezing and thawing conditions, unexpected crystallization of excipients within the bulk drug substance, pH-shift of the buffer during freezing, and long lag time due to thawing, e.g., a 2 liter container at temperatures of approximately 37° C. Using spray-dried bulk drug compositions can avoid these problems. Further, spray dried bulk drug compositions are very convenient to handle during compounding of the final drug product composition, and allows the manufacture of a broad concentration range. Additionally, spray dried drug compositions, where only water is added, may supersede classical compounding and therefore decrease risk during drug product manufacturing while increasing output capacity. Further, full length/complete antibodies may be less prone to physical degradation compared to monoclonal antibody (mAb) fragments. In addition, there is typically little or no increase in physical or chemical degradation with increase of protein concentration up to 100 mg/mL. Since higher concentrated solutions will increase the efficiency of the process, the use of 100 mg/mL protein concentrations will be beneficial.

BRIEF DESCRIPTION OF THE DRAWINGS

These and other features and advantages of the methods and compositions disclosed herein will be more fully understood by reference to the following detailed description in conjunction with the attached drawings, in which.

DETAILED DESCRIPTION OF THE INVENTION

I. Definitions

Figure 1:
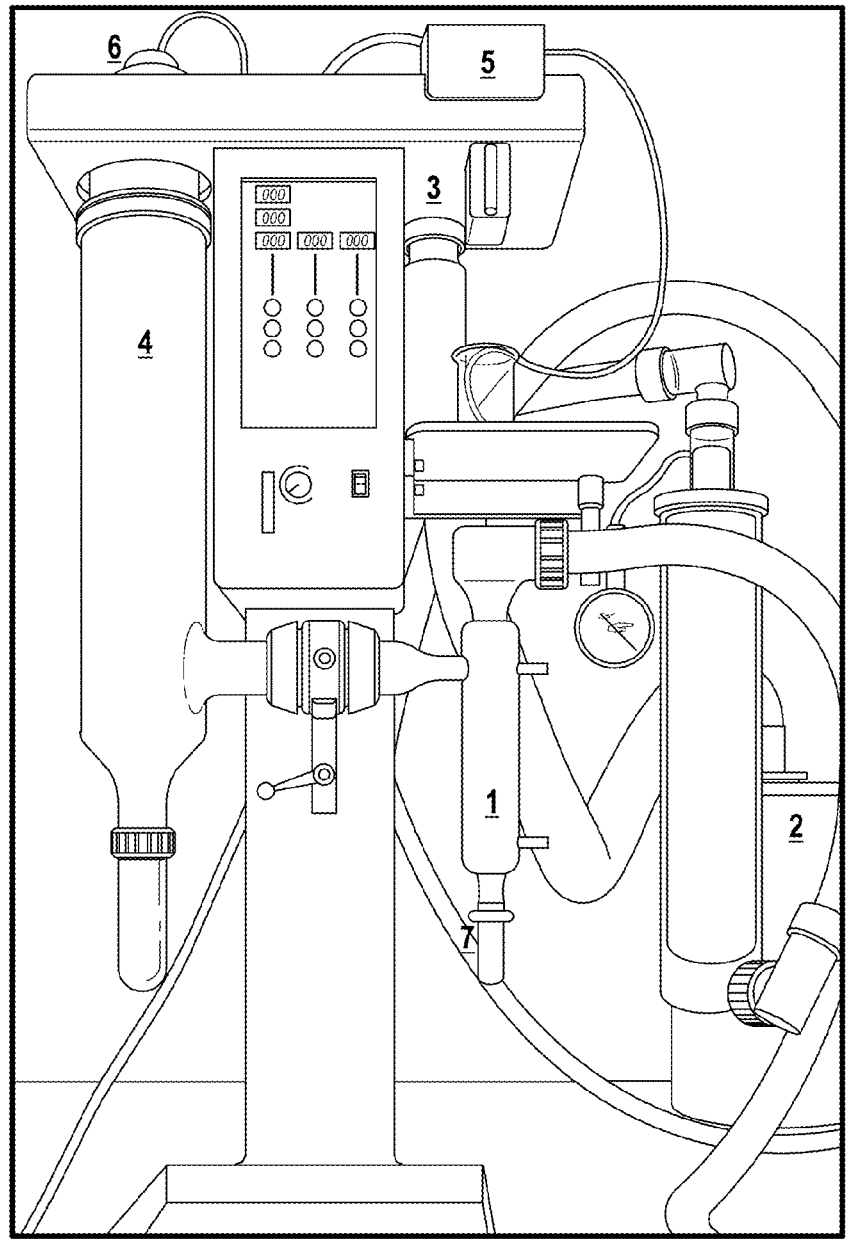
FIG. 1 depicts a Büchi spray dryer B-191 as used in the examples.

In order that the present invention may be more readily understood, certain terms are first defined.

As used herein, the term "acidic component" refers to an agent, including a solution, having an acidic pH, i.e., less than 7.0. Examples of acidic components include phosphoric acid, hydrochloric acid, acetic acid, citric acid, oxalic acid, succinic acid, tartaric acid, lactic acid, malic acid, glycolic acid and fumaric acid.

As used herein, the term "antioxidant" is intended to mean an agent that inhibits oxidation or acts as an antioxidant synergist and thus is used to prevent the deterioration of preparations by the oxidative process. Such compounds include by way of example and without limitation, Alpha tocopherol (Vitamin E), ascorbic acid, ascorbyl palmitate, citric acid, butylated hydroxyanisole, butylated hydroxytoluene, edetic acid (EDTA, edetate) and salts thereof, hydrophosphorous acid, malic acid, monothioglycerol, propionic acid, propyl gallate, methionine, sodium ascorbate, sodium citrate, sodium sulfide, sodium sulfite, sodium bisulfite, sodium metabisulfite, and others known to those of ordinary skill in the art.

Unless otherwise indicated herein, the terms "composition" and "formulation" are used interchangeably.

The term "excipient" refers to an agent that may be added to a formulation to provide a desired consistency, e.g., altering the bulk properties, to improve stability, and/or to adjust osmolality. Examples of commonly used excipients include, but are not limited to, stabilizing agents, sugars, polyols, amino acids, surfactants, chelating agents and polymers.

The term "pharmaceutical" as used herein with reference to a composition, e.g., an aqueous formulation, is one that is useful for treating a disease or disorder.

The term "protein" is meant to include a sequence of amino acids for which the chain length is sufficient to produce the higher levels of secondary and/or tertiary and/or quaternary structure. This is to distinguish from "peptides" or other small molecular weight molecules that do not have such structure. Examples of proteins encompassed within the definition used herein include therapeutic proteins. A "therapeutically active protein" or "therapeutic protein" refers to a protein that may be used for therapeutic purposes, i.e., for the treatment of a disorder in a subject. It should be noted that while therapeutic proteins may be used for treatment purposes, the invention is not limited to such use, as the proteins may also be used for in vitro studies. In a preferred embodiment, the therapeutic protein is a fusion protein or an antibody, or antigen-binding portion thereof. In one embodiment, the methods and compositions of the invention comprise at least two distinct proteins, which are defined as two proteins having distinct amino acid sequences. Additional distinct proteins do not include degradation products of a protein.

The term "protein powder" refers to a composition comprising a protein that is made according to the spray drying methods of the invention. An "antibody powder" refers to a composition including an antibody, or an antigen-binding portion thereof, that is made according to the spray-drying methods of the invention.

The term "pharmaceutical formulation" refers to preparations that are in such a form as to permit the biological activity of the active ingredients to be effective, and, therefore, may be administered to a subject for therapeutic use.

The term "solution" refers to a mixture of at least one excipient or protein or peptide within a liquid. The solution can include dissolved protein molecules, colloidal dissolved protein molecules, dispersed protein aggregates or crystals or precipitates or suspensions within the liquid, or combinations thereof.

A "stable" composition is one in which the protein therein, for example, essentially retains its physical stability and/or chemical stability and/or biological activity during processing and/or upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. In one embodiment, the stability of the protein is determined according to the percentage of monomer protein in the solution, with a low percentage of degraded (e.g., fragmented) and/or aggregated protein. For example, an aqueous composition including a stable protein may include at least 95% monomer protein. Alternatively, an aqueous composition of the invention may include no more than 5% aggregate and/or degraded protein.

The term "stabilizing agent" refers to an excipient that improves or otherwise enhances stability. Stabilizing agents include, but are not limited to, α-lipoic acid, α-tocopherol, ascorbyl palmitate, benzyl alcohol, bisulfites, boron, butylated hydroxyanisole (BHA), butylated hydroxytoluene (BHT), ascorbic acid and its esters, carotenoids, calcium citrate, acetyl-L-carnitine, chelating agents, chondroitin, chondroitin sulfate, citric acid, coenzyme Q-10, EDTA (ethylenediaminetetraacetic acid; edetate disodium), erythorbic acid, fumaric acid, alkyl gallates, glucosamine (chitosan, sodium hyaluronate), malic acid, metabisulfite, propyl gallate, sodium bisulfite, sodium metabisulfite, sodium sulfite, potassium sulfite, tartaric acid, thiosulfates, thioglycerol, tocopherol and their esters, e.g., tocopherol acetate, tocopherol succinate, tocotrienal, d-α-tocopherol acetate, vitamin C and its esters, vitamin E and its esters, e.g., vitamin E acetate, and combinations thereof.

As used herein, the term "tonicity modifier" is intended to mean a compound or compounds that can be used to adjust the tonicity of a liquid formulation. Suitable tonicity modifiers include glycerin, lactose, mannitol, dextrose, sodium chloride, magnesium sulfate, magnesium chloride, sodium sulfate, sorbitol, trehalose, sucrose, raffinose, maltose and others known to those or ordinary skill in the art. In one embodiment, the tonicity of the liquid formulation approximates that of the tonicity of blood or plasma.

The term "antibody" as referred to herein includes whole antibodies and any antigen binding fragment (i.e., "antigen-binding portion") or single chains thereof. An "antibody" refers to a glycoprotein generally including at least two heavy (H) chains and two light (L) chains inter-connected by disulfide bonds, or an antigen binding portion thereof. The term "antibody" also includes isolated naturally occurring variants thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., TNFα, IL-12, IL-13). The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment including two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ or $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. In one embodiment of the invention, the antibody fragment is selected from the group consisting of a Fab, an Fd, an Fd', a single chain Fv (scFv), an scFv$_a$, and a domain antibody (dAb).

Still further, an antibody or antigen-binding portion thereof may be part of a larger immunoadhesion molecule, formed by covalent or noncovalent association of the antibody or antibody portion with one or more other proteins or peptides. These other proteins or peptides can have functionalities that allow for the purification of antibodies or antigen-binding portions thereof or allow for their association with each other or other molecules. Thus, examples of such immunoadhesion molecules include use of the streptavidin core region to make tetrameric single chain variable fragment (scFv) molecules (Kipriyanov et al. (1995) *Human Antibodies and Hybridomas* 6:93-101) and the use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Two antibody domains are "complementary" where they belong to families of structures that form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the Vα and Vβ (or gamma and delta) domains of the T-cell receptor.

The term "domain" refers to a folded protein structure that retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

Variable domains of the invention may be combined to form a group of domains; for example, complementary domains may be combined, such as $V_L$ domains being combined with $V_H$ domains. Non-complementary domains may also be combined. Domains may be combined in a number of ways, involving linkage of the domains by covalent or noncovalent means.

A "dAb" or "domain antibody" refers to a single antibody variable domain ($V_H$ or $V_L$) polypeptide that specifically binds an antigen.

As used herein, the term "antigen binding region" or "antigen binding site" refers to the portion(s) of an antibody molecule, or antigen binding portion thereof, which contains the amino acid residues that interact with an antigen and confers on the antibody its specificity and/or affinity for the antigen.

The term "epitope" is meant to refer to that portion of any molecule capable of being recognized by and bound by an antibody at one or more of the antibody's antigen binding regions. In the context of the present invention, first and second "epitopes" are understood to be epitopes that are not the same and are not bound by a single monospecific antibody, or antigen-binding portion thereof.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The term "human antibody" refers to antibodies having variable and constant regions corresponding to, or derived from, human germline immunoglobulin sequences as described by, for example, Kabat et al. (See Kabat, et al. (1991) Sequences of Proteins of Immunological Interest, Fifth Edition, U.S. Department of Health and Human Services, NIH Publication No. 91-3242). The human antibodies of the invention, however, may include amino acid residues not encoded by human germline immunoglobulin sequences (e.g., mutations introduced by random or site-specific mutagenesis in vitro or by somatic mutation in vivo), for example the CDRs and in particular CDR3.

Recombinant human antibodies of the invention have variable regions, and may also include constant regions, derived from human germline immunoglobulin sequences (See Kabat et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. In certain embodiments, however, such recombinant antibodies are the result of selective mutagenesis or backmutation or both.

The term "backmutation" refers to a process in which some or all of the somatically mutated amino acids of a human antibody are replaced with the corresponding germline residues from a homologous germline antibody sequence. The heavy and light chain sequences of a human antibody of the invention are aligned separately with the germline sequences in the VBASE database to identify the sequences with the highest homology. Differences in the human antibody of the invention are returned to the germline sequence by mutating defined nucleotide positions encoding such different amino acid(s). The role of each amino acid thus identified as candidate for backmutation should be investigated for a direct or indirect role in antigen binding and any amino acid found after mutation to affect any desirable characteristic of the human antibody should not be included in the final human antibody. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmutation may occur at any stage of antibody optimization.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of $V_H$ and/or $V_L$ are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the $V_H$ and/or $V_L$ sequence has been altered to be more "human-like", i.e., more similar to human germline variable sequences. One type of humanized antibody is a CDR-grafted antibody, in which human CDR sequences are introduced into non-human $V_H$ and $V_L$ sequences to replace the corresponding nonhuman CDR sequences.

Various aspects of the invention are described in further detail in the following subsections.

II. Methods of the Invention

The methods of the present invention and the resulting compositions of the present invention offer multiple advantages for drug substance shipping and/or distribution, e.g., the preparations are lightweight and stabile at ambient temperature. There are also advantages for drug compounding and/or manufacturing, e.g., no lengthy thawing of bulk solutions at controlled rates. One readily can weigh out the dry protein powders of the present invention in amounts sufficient for the desired concentrations, and mix or compound with the desired excipients such as water. The separation and drying of protein precipitates or protein crystal suspension is also not necessary as with conventional preparations. There are additional advantages for drug product development with regard to the ability to attain high concentration formulations, improved bioavailability, local release (e.g., pulmonary delivery), sustained release (e.g., liposomes and PLGA-coated microspheres) and new solid or hydrogel protein dosage forms that can be administered in a variety of ways, including orally and topically. Accordingly, in some embodiments the methods also include further processing, e.g., incorporation of the powdered compositions into coated sustained-release compositions, liposomes, PLGA-coated microspheres, incorporation within excipient matrices by melt extrusion and the like. The resulting compositions are also further embodiments of the present invention, e.g., sustained release or targeted compositions and/or compositions that allow for alternative administration routes, e.g., oral, dermal and enteral administration. Another advantage is that the compositions of the present invention can be processed at higher temperatures than conventional preparations. For example, the powders can be processed by a melt extrusion technology, such as the MELTREX melt extrusion technology.

In one aspect, the present invention provides methods of efficiently and effectively preparing stable powders that include one or more proteins or peptides. In certain embodiments, the proteins or peptides are antibodies and/or an antigen binding portion thereof. The method for preparing the powder includes spray drying a solution of a protein, peptide, antibody or antigen binding portion thereof. For example, the solution can include at least about 50 mg/mL of the protein, peptide, antibody or antigen binding portion thereof. In further embodiments, the solution can have a different concentration, e.g., be more concentrated, e.g., the solution can include at least about 40 mg/mL, 50 mg/mL, 60 mg/mL, 70 mg/mL, 80 mg/mL, 90 mg/mL, 100 mg/mL, 130 mg/mL, 150 mg/mL, 180 mg/mL, etc. of the protein, peptide, antibody or antigen binding portion thereof. The solution may also include one or more excipients. The method can include concentrating or further concentrating the solution by any known method, including, e.g., ultrafiltration. The protein or peptide can be any suitable protein or peptide. The protein may be an antibody, or antigen binding portion thereof, e.g., an immunoglobulin G (IgG) antibody or antigen binding portion thereof. In certain embodiments, the antibody, or antigen binding portion thereof, is MAK 195F, Adalimumab, ABT-325, ABT-308 or ABT-147.

In some embodiments, the solution includes an excipient. Suitable excipients include, but are not limited to, trehalose, sucrose, sorbitol, polyethylene glycol, at least one amino acid, histidine, alanine, arginine, glycine, or a mixture thereof. The method can further include adding an acidic component, antioxidant, and/or tonicity modifier to the solution or the powder.

The solution can include between about 15 and about 140 mM, or between about 20 and about 30 mM excipient. In certain embodiments, the solution includes about 25 mM excipient. In some embodiments, the solution comprises an excipient:protein ratio of between about 0.27:1.0 and about 2.8:1.0, between about 0.27:1.0 and about 1.4:1.0, or between about 0.27:1.0 and about 0.7:1.0. In certain embodiments, the solution comprises an excipient:protein ratio of about 0.7:1.0.

In some embodiments, the solution has a low percentage of protein aggregates, despite the high concentration of the aqueous protein formulation. In one embodiment, the aqueous solution including water and a high concentration of a protein, e.g., antibodies, contains less than about 5% protein aggregates, even in the absence of a surfactant or other type of excipient. In one embodiment, the solution comprises no more than about 7.3% aggregate protein; the solution comprises no more than about 5% aggregate protein; the solution comprises no more than about 4% aggregate protein; the solution comprises no more than about 3% aggregate protein; the solution comprises no more than about 2% aggregate protein; or the solution comprises no more than about 1% aggregate protein. In one embodiment, the solution comprises at least about 92%, at least about 93%, at least about 94%, at least about 95%, at least about 96%, at least about 97%, at least about 98%, or at least about 99% monomer protein. Ranges intermediate to the above recited concentrations, e.g., at least about 98.6% monomer protein, no more than about 4.2% aggregate protein, are also intended to be part of this invention. In addition, ranges of values using a combination of any of the above recited values as upper and/or lower limits are intended to be included.

In some embodiments, the inlet air temperature ($T_{in}$) is between about 105° C. and about 175° C., between about 130° C. and about 155° C., between about 120° C. and about 160° C., or between about 125° C. and about 160° C. In certain embodiments, the $T_{in}$ is about 130° C. In some embodiments, the outlet air temperature ($T_{out}$) is between about 60° C. and about 112° C., between about 60° C. and about 90° C., between about 70° C. and about 90° C., or between about 75° C. and about 85° C. In certain embodiments, the $T_{out}$ is about 80° C.

In some embodiments, the methods of the invention include spray drying with an inlet air temperature ($T_{in}$) between about 100° C. and about 180° C., and an outlet air temperature ($T_{out}$) between about 60° C. and about 110° C.

In certain embodiments, the method includes spray drying with a $T_{in}$ of about 130° C. and a $T_{out}$ of about 80° C.

In some embodiments the residual moisture content of the resulting powdered composition is between about 1% and about 3%, between about 1.5% and 2.5%, between about 1.4% and about 2%, between about 4% and about 6%, or between about 4.5% and about 5%. In other embodiments the powdered composition includes about 1%, 1.5%, 2%, 2.5%, 3%, 3.5%, 4%, 4.5%, 5%, 5.5%, 6%, 6.5%, or 7% residual moisture.

In one embodiment, the powder is stable at ambient temperatures and humidity for at least 3 months. In some embodiments, the powder is stable for at least 6 months, 9 months, 1 year, 2 years, 3 years or 5 years at ambient temperatures and humidity. In other embodiments, the powder is stable at 40° C. for at least 3 months. In additional embodiments, the powder is stable at 40° C. for at least 3 months, 6 months, 9 months, 1 year, 2 years or 5 years.

In some embodiments, spray drying includes atomizing the solution to form solution droplets, drying the droplets with a gas to form a powder, and recovering the powder from the gas. The solution can be atomized employing, e.g., a pressure nozzle atomizer. The powder can be recovered employing, e.g., a cyclone. Exemplary methods of spray drying are discussed and exemplified herein.

In another aspect, the invention provides a method for preparing a pharmaceutical preparation that can include any of the methods described herein for preparing a powder, and further includes mixing (e.g., embedding or dissolving) the powder with a pharmaceutically acceptable carrier. The pharmaceutically acceptable carrier can be any carrier acceptable for parental, oral, enteral, or topical administration. The carrier can be solid, semi-solid or liquid (e.g., water) or combinations thereof.

In some embodiments, the method includes dissolving the antibody, or antigen binding portion thereof, powder in a pharmaceutically acceptable carrier. The pharmaceutically acceptable carrier may be, e.g., acceptable for parental administration, and may include, e.g., water. The method can further include adding one or more acidic components, antioxidants, and/or tonicity modifiers to the pharmaceutical composition. Additionally or alternatively, suitable additives can be added to the pharmaceutical compositions of the invention, e.g., buffers, viscosity modifiers, flavorants, colorant, etc.

The method can include further processing a stable powdered composition of the invention at a temperature above ambient temperature without significantly affecting the stability of the powdered compositions. For example, the method can include melt extruding the stable powdered composition.

In some embodiments, one or more coatings are applied to the powdered composition, e.g., such that discreet particles or aggregates of particles are coated and/or such that a composite of particles, e.g., a pressed tablet, is coated. The coating can include any coating commonly used and known in the art. Such coatings can include polymers, such as PLGA to form a sustained release or delayed release pharmaceutical composition. The coatings can be or include an enteric coating. The composition can be encapsulated, e.g. in a gelatin capsule, or be suspended in a hydrogel. In certain embodiments, the activity of the protein, peptide, antibody, or antigen binding portion thereof, is thus or otherwise protected by the excipient against precipitation, denaturation or oxidation by organic solvents thereby allowing coating with substances such as PLGA that are only soluble in organic solvents. Such solvents can include solvents commonly found in pharmaceutical preparations, including, but not limited to, a polyethylene glycol (e.g., a low molecular weight such as PEG 400), ethanol, dimethyl sulfoxide (DMSO), N-methylpyrrolidone (NMP), or glacial acetic acid.

Spray Drying

In a spray dryer, a pumpable fluid (solution, suspension, emulsion or paste) is transformed into a dried particulate form. The process combines particle formation and drying in one step by atomizing the liquid feed into a hot drying medium (normally air or inert gases). In some embodiments of the present invention, concentrated protein solutions are spray dried. Accordingly, the methods of the invention can include concentrating protein solutions employing any suitable method. In some embodiments, Tangential Flow Filtration (TFF) technique is employed, since this is a very rapid and gentle method. However, additionally or alternatively, normal flow filtration or dialysis can be used.

Atomization of the fluid results in an increase of the liquid's surface and therefore leads to very short drying times. For example, decreasing the droplet size from 10 μm to 1 μm results in an increase in surface area from 600 to 6000 $m^2$ and shortens its drying time by a factor 100 (from 0.01 s to 0.0001 s). Stahl, Feuchtigkeit und Trocknen in der Pharmazeutischen Technologie. Dr. Dieter Steinkopf Verlag GmbH & Co. KG, Darmstadt (1999).

The contact between the liquid feed and the drying air can occur in two different modes. In a co-current system, drying air and particles (droplets) move through the drying chamber in the same direction. This is the preferred mode for heat sensitive material (such as proteins), because the hottest air contacts the moist droplets. When drying air and droplets move in an opposite direction, this is called a counter-current mode. Particles produced in counter-current mode usually show a higher temperature than the exhausting air. The exhausted air itself can leave the system ("open-cycle") or can be recirculated ("closed-cycle", generally used for evaporating organic solvents with inert gases). Spray Drying Process Principles (the Niro website, February 2007). By choosing from the various spray dryer designs (size, atomizer, aseptic conditions, etc.) and adjusting the different process parameters (drying air flow, drying air temperature, etc.), the final powder properties like particle size, shape and structure or even sterility can be controlled. If the resulting moisture of the recovered powder is not sufficiently low, post-treatment might be required, e.g., in the form of fluid bed dryers and coolers, contact dryers or even microwave dryers. Masters, Spray Drying in Practice. SprayDryConsult International ApS; Charlottenlund (2002).

The spray drying process generally includes: atomization of the liquid feed; drying of the droplets; and separation and recovery of the dried product. Each step has its own influence on the resulting product and also provides difficulties, especially when dealing with sensitive material like proteins.

In order to spray dry a protein or peptide it is often advantageous to use stabilizing adjuvants. Sugars such as trehalose and sucrose are effective protein stabilizers. Not only can they reduce aggregation and/or inactivation of proteins during the spray drying process, they can also have positive effects on the storage stability of the resulting powder, if stored below its glass transition temperature. Lee, *Rational Design of Stable Protein Formulations, Theory and Practice* (Kluwer Academic/Plenum Publishers, 2002).

Atomization is the fragmentation of a liquid into a multitude of single droplets, the so-called spray. The choice of atomization device effects the final product quality and throughput. Richter, *Verfahrenstechnik, Sonderausgabe Martübersicht* 11: 96-100 (1997). Common to all atomizers is the use of energy to break up a liquid. Different kinds of energy distinguish the different atomizers. The energy leads to turbulence in the issuing liquid. Together with applied air forces, the surface tension and viscosity of the liquid are overcome and disintegration takes place.

For spray drying operations, the most suitable spray is one of small droplets of more or less equal size. Not all atomization systems can provide a narrow particle size distribution for spray dried powders. Masters, Spray Drying in Practice. SprayDryConsult International ApS; Charlottenlund (2002). Proteins are very sensitive materials, so atomization represents a stress factor as it implicates shear forces, a possible cause of instability. Mahler et al. found a correlation between high shear forces (stirring and shaking) and an aggregation increase of an IgG1 solution. Mahler et al., *Eur. Journal of Pharm. and Biopharm.* 59: 407-417 (2005). A lysozyme solution also showed aggregation and loss of activity during atomization. Yu et al., *Eur. Journal of Pharm. Sci* 27: 9-18 (2006). Shear stress and the abrupt enlargement of the liquid/air interface seem to be responsible for this kind of protein deterioration. Maa et al., *Biotechnology and Bioengineering* 54(6): 503-512 (1997). But even shear forces that occur in pumping procedures can suffice to stress a protein solution. Brennan et al., *Diabetes* 34, 353-359 (1985). Many different types of atomizers are available for spray drying procedures.

Rotary atomizers accelerate the liquid feed centrifugally before it is discharged into the air/gas atmosphere. The liquid feed is distributed centrally on a spinning wheel, disc or cup. At low disc speed the formation of droplets is mainly dependent on viscosity and surface tension of the liquid. The higher the disc speed, the more inertia and air friction come into play and contribute to the mechanism of droplet formation. Moreover, droplet size is influenced by the liquid feed rate, its solid content and density, the atomizer disc diameter and design. Different designs of rotary atomizers are available: vaneless discs/bowls/cups or vaned wheels with curved or straight vanes. Masters, Spray Drying Handbook (Wiley & Sons Inc., New York, 1991).

Rotary atomizers have a spray angle of 360° and hence require a certain diameter of the drying chamber (to minimize wall deposition). These systems are normally used for higher capacities.

The pressure nozzle systems obtain all the energy required for discharging the liquid from the liquid itself by converting pressure energy into kinetic energy. The simplest one-fluid nozzle is a tubular capillary used to drip out single droplets. This device is only used for generating small amounts of equal droplets. By increasing the flow rate atomization can be achieved, wherein the liquid jet is fragmented into droplets via turbulence. Disintegration of the fluid can be ameliorated by making the liquid undergo deflections, rotations and turns, e.g., by providing the nozzle with swirl inserts or swirl chambers. Resulting droplet size is influenced by the applied pressure and the nozzle diameter, in addition to the previously discussed parameters (viscosity, flow rate, etc.). Richter, *Verfahrenstechnik, Sonderausgabe Martübersicht* 11: 96-100 (1997). The liquid feed leaves the orifice as a hollow cone, i.e., pressure nozzles can be used in small spray drying installations with low diameter drying chambers. Large numbers of different nozzle designs offer variable applications for atomizing solutions, emulsions and suspensions, only limited by particle size (suspensions) and viscosity (very high pressure required). Masters, Spray Drying in Practice. SprayDryConsult International ApS; Charlottenlund (2002).

When employing pneumatic nozzle atomization, the impaction of a high velocity gaseous medium (usually air) with the liquid provides the energy for droplet formation. Depending on the place where fluid and gas collide, internal-mixing and external-mixing systems are distinguished. Richter, *Verfahrenstechnik, Sonderausgabe Martübersicht* 11: 96-100 (1997). Two fluid nozzles are preferably used when highly viscous fluids have to be broken up into fine sized droplets. The gaseous medium is pressurized inside the nozzle (up to 7 bar), which is sometimes equipped with an additional swirl insert to generate gas turbulences facilitating the disintegration of the liquid feed. The latter is normally pumped by low pressure pumps supporting the air-flow ejector effect. Pneumatic nozzle systems produce droplets in a range of 5 to 75 µm. Disadvantages are the high costs for compressed gas/air and its cooling effect inside the drying chamber. When handling liquids with very high viscosity, there is also the danger of blocking the nozzle orifice. Masters, Spray Drying in Practice. SprayDryConsult International ApS; Charlottenlund (2002).

Ultrasonic nozzles employ high frequency sound waves to achieve atomization. Piezoelectric transducers receive high frequency electrical energy from an Ultrasonic Generator and convert it into vibratory mechanical motion at the same frequency. Liquid is introduced running the length of the nozzle. When the liquid feed reaches the orifice it absorbs the vibrational energy, causing it to atomize. Sono Tek Corporation: Ultrasonic spray nozzle systems (SONO TEK Corporation, New York, 2007).

Sonic nozzles work at low pressures (especially compared to pneumatic nozzles) and the resulting droplets have a diameter between 10 and 50 µm. One big disadvantage of using ultrasonic atomizers is the unpredictability of continuous operation, e.g., when used for solid-containing feedstocks, the risk of pre-drying in the nozzle area could lead to fouling of the generator/atomization process. Therefore these systems are more often used in lab-scale and pilot dryers for generating fine sprays or when non-Newtonian or highly viscous liquids do not allow use of other nozzle systems. Masters, Spray Drying in Practice. SprayDryConsult International ApS; Charlottenlund (2002).

Predicting the drying kinetics of sprays during spray drying is complicated by both the difficulties in monitoring the behavior of a whole spray and the non-uniform conditions inside the drying chamber. Drying kinetics of single droplets can, however, be studied theoretically and practically. Elversson et al., *Journal of Pharm. Sci* 94(9): 2049-2060 (2005).

As soon as the liquid feed is atomized, its surface to mass ratio is increased and the heat transfer between the air and the droplets is accelerated, and droplets can now dry very fast. At common droplet sizes of <100 µm, evaporation takes place within less than 1 s. Nürnberg et al., *Acta Pharmaceutica Technologica*, 26 (1): 39-67, Tab 3-1 (1980). Two convection processes are involved: heat transfer (air→droplet) and mass transfer of moisture (droplet→air). In the latter, moisture has to permeate through the boundary layer that surrounds each droplet. Transfer rates are influenced by temperature, humidity, transport properties of the surrounding air, droplet diameter and relative velocity between droplet and air. Masters, Spray Drying Handbook (Wiley & Sons Inc., New York, 1991). At first, evaporation takes place at a constant rate (first stage of drying=constant rate period). Diffusion of moisture from within the droplet maintains saturated surface conditions. At the so-called "critical point", the moisture content becomes too low to maintain saturation on the droplet surface, and a dry layer starts to form at the droplet's surface. From then on there is an additional growing barrier to cross by diffusion. As a result of the permanently changing conditions of the droplet/particle, the evaporation rate decreases (falling rate period=second stage of drying). Masters, Spray Drying in Practice. SprayDryConsult International ApS; Charlottenlund (2002). The temperature of the droplets/particles during the process is mainly influenced by the inlet drying air temperature ($T_{In}$) and the liquid feed rate ($Q_{LF}$), to some extent by the drying air flow rate ($Q_{DA}$) and the atomizing air flow rate ($Q_{AA}$). These four parameters also determine $T_{Out}$. In practice, the temperature just below the nozzle orifice is much closer to $T_{Out}$ than to $T_{In}$, so $T_{Out}$ seems to be the dominating variable for the droplet drying rate. Of course the temperature inside the droplet ($T_i$) is lower than on its surface ($T_s$). $T_s$ soon reaches the wet bulb temperature, $T_{wb}$, and stays there during the constant rate period. With the growing crust on the droplet surface in the falling rate period, $T_s$ and $T_i$ begins to increase. Maa et al., *Biotechnology and Bioengineering* 53 (6):503-512 (1997). For the resulting particle morphology droplet size, as well as the texture of the crust, play a crucial role. Elversson et al. postulated a linear relationship between droplet size and particle size, but also suggested that solid content in the liquid feed influences particle size strongly. Elversson et al., *Journal of Pharm. Sci.* 92(4): 900-910 (2003).

Drying implies two more stress factors for proteins: heat and dehydration. Protein stability to thermal stress is a crucial variable in protein formulation. Changes in temperature during the spray drying process have great impact on the protein stability (e.g., process-stability, shelf-life during accelerated stability testing). When exposed to elevated temperatures proteins become more flexible (hydrogen bonds are weakened), leading to partial unfolding, and their collision frequency increases. Brange, Pharmaceutical Formulation Development of Peptides and Proteins (Taylor & Francis Ltd., 2000). This process is usually reversible, but once partially unfolded, proteins are very susceptible to further degradation pathways like aggregation or incorrect folding, which strongly impact their function and long-term stability.

The temperature for maximum stability is between −10 and 35° C. for most proteins. Bummer et al., *Protein Formulation and Delivery* (Marcel Dekker AG, Basel, 2000). Mumenthaler et al. assumed that the drying particles reach a maximum temperature of about 25° C. below $T_{Out}$. Mumenthaler et al., *Pharm. Res.* 11(1): 12-20 (1994). In the present invention, $T_{Out}$ can range from about 60° C. to approximately 80° C. Heat denaturation is generally not considered to be the main instability factor during spray drying. Maa et al., *Current Pharmaceutical Biotechnology* 1(3):283-302 (2000).

Biological activity of proteins depends on their native, three-dimensional structure. In an aqueous solution, proteins maintain their native structure by being surrounded by non-covalently bound water molecules on their surface. Normally the non-polar amino acid residues are buried in the interior and the polar amino acid residues are present on the surface. This leads to a very close package of proteins in solution (higher packing density than in crystals of organic molecules). Brange, Pharmaceutical Formulation Development of Peptides and Proteins (Taylor & Francis Ltd., 2000). Removing the water can destabilize this package, and conformational changes can occur.

The last step of a spray drying process is typically the separation of the powder from the air/gas and the removal of the dried product. In some embodiments, this step is as effective as possible to obtain high powder yields and to prevent air pollution through powder emission to the atmosphere. To this end, dry and wet collection equipment can be used, like cyclones, bag filters or electrostatic precipitators. Even combinations of these units can be installed. Masters, Spray Drying in Practice. SprayDryConsult International ApS; Charlottenlund (2002). Because of its simple design and its effectiveness, the cyclone separator is one of the most common separators and is used in various industries. Coulson and Richardson, *Chemical Engineering*, 4th, Vol. 2 (Butterworth-Heinemann, Oxford, 1991). Particle movement inside the cyclone is the result of two opposing forces. The centrifugal force moves the particles to the cyclone wall, while the drag force of the air/gas tries to carry the particles into the central air core to leave the cyclone. Masters, Spray Drying in Practice. SprayDryConsult International ApS; Charlottenlund (2002). Powder and air enter the cyclone tangentially and swirl in a spiral form downwards to the bottom of the cyclone (outer vortex). At this point most particles leave the cyclone to be collected in a bottom-mounted vessel, the air containing only the fine particle fraction and other particles that could not be separated spirals upwards in the center (inner vortex) of the cyclone and passes out of the top. In practice, particle sizes above 30 µm should be recovered, which are also dependent on the dimensions of the spray dryer. Masters, Spray Drying in Practice. SprayDryConsult International ApS; Charlottenlund (2002). However, yield can be optimized by varying the cyclone dimensions. Maury et al. achieved much higher yields with a newly developed cyclone separator on a Büchi B-191 spray dryer compared to the standard cyclone. Maury et al., *Eur. Journal of Pharm. and Biopharm.* 59(3): 565-573 (2005). The high performance cyclone (small diameter) separated more, including even very small particles (diameter below 1.5 µm).

Theoretical work has been performed on calculating cyclone efficiency. One approach is to calculate the so called "cut-off point", e.g., by the following equation:

$$d_p^* = \sqrt{\frac{18\eta r_i v_{ri}}{(\rho_s - \rho_g) u_i^2}}$$

$d_p^*$ is the cut-off particle diameter, $\eta$ is the air viscosity, $r_i$ stands for the radius of the inner vortex, $v_{ri}$ is the radial air velocity at the air inlet, $\rho_s$ and $\rho_g$ represent the densities of the solid and the gas, $u_i$ is the tangential particle velocity at $r_i$. At this point (diameter of the particle) centrifugal force and drag force have equal values. Particles of that size rotate without tendency to the inner or outer vortex, smaller particles are swept along by the exhausting air, larger particles fall into the collecting vessel. Staudinger et al., *VDI Berichte* 1511: 1-23 (1999).

The time-of-flight approach is another way to calculate the critical particle diameter. It takes into consideration how long it takes a particle to travel to the cyclone wall. In this approach the geometry of the collecting vessel can be taken into account, because it influences the gas stream inside the cyclone. Qian et al., *Chem. Eng. Technol.* 29(6): 724-728 (2006).

Spray drying an aqueous protein solution without any adjuvants normally leads to unfolding, aggregation and inactivation. It has been tried several times with various proteins: oxyhemoglobin (Labrude et al.), trypsinogen (Tzannis et al.), IgG (Maury et al. 2005) and in all cases process instability was observed. Labrude et al., *Journal of Pharm. Sci.* 78 (3): 223-229 (1989), Tzannis, et al., *Journal of Pharm. Sci.* 88(3): 351-359 (1999), and Maury et al., *Eur. Journal of Pharm. and Biopharm.* 59(2):251-261 (2005). Accordingly, in some embodiments, the compositions of the invention protect the active pharmaceutical ingredient (API) during the spray drying process and also during storage. In the freeze drying of proteins, sugars (trehalose, sucrose), amino acids (arginine) or surfactants (Tween) have been employed as stabilizing agents. Lee, *Rational Design of Stable Protein Formulations, Theory and Practice* (Kluwer Academic/Plenum Publishers, 2002). For the use of polyols, disaccharides and amino acids, several stabilizing theories have been proposed. One of them is the so-called "preferential exclusion" theory, established by Arakawa and Timasheff. Arakawa et al., *Biochemistry* 21: 6536-6544 (1982), Arakawa et al., *Advanced Drug Delivery Reviews* 46: 307-326 (2001), and Timasheff, *Annual Reviews Biophys. Biomol. Struct.* 22: 67-97 (1993). It is based on the premise that proteins are preferentially hydrated in solution, so the co-solutes are excluded from contact with the protein surface. As unfolding would lead to a greater protein surface, the area from which the co-solvent has to be excluded would be greater as well. In this case, unfolding leads to a thermodynamically unfavorable situation, hence the protein remains in its folded natural conformation. Arakawa et al., *Advanced Drug Delivery Reviews* 46: 307-326 (2001). Proteins can also be protected by the "water replacement" mechanism. This theory says that the excipients prevent unfolding by hydrogen bonding to the dried protein instead of the evaporated water. Carpenter et al., Rational Design of Stable Protein Formulations, Theory and Practice (Kluwer Academic/Plenum Publishers, 2002). Also, formation of a glassy matrix that immobilizes the protein can be a reason for protein stability upon drying and storage. Tzannis et al., *Journal of Pharm. Sci.* 88(3): 360-370 (1999). Therefore, formulations are needed that exhibit a high glass transition temperature (Tg), e.g., a Tg higher than the storage temperature to impede molecular motion. The stabilization mechanism of surfactants is based on the competition of surfactants and proteins to occupy interfaces (e.g., liquid/air interface), showing a thermodynamic edge to the surfactant. With a small chance for the protein to adsorb at the interface, the risk of unfolding and aggregation is significantly reduced. Adler et al., *Journal of Pharm. Sci.*, 88 (2), 199-208 (1999).

Humidity is another factor influencing protein stability, especially during long term storage. The impact of moisture on protein powders is well documented in the literature. Normally, the chemical stability of a solid protein formulation decreases with increasing moisture content due to water serving as a reactant or as a medium for mobilization of reactants. It can also be responsible for conformational changes in the protein structure. Besides that, the Tg of the spray dried powders is also influenced by water. Water acts as a plasticizer, which means it lowers the Tg of a substance. The influence of water can be calculated using the Gordon Taylor Equation, an equation to calculate the Tg of binary mixtures ($T_{gmix}$).

$$T_{gmix} = (\omega_1 \cdot T_{g1} + K \cdot \omega_2 \cdot T_{g2})/(\omega_1 + K \cdot \omega_2)$$

$$K = (\rho_1 \cdot T_{g1})/(\rho_2 \cdot T_{g2})$$

$\omega$, Tg, and $\rho$ represent weight fraction, glass transition temperature and density of the different components, respectively. For water having a Tg of approximately −138° C. it is evident that the water content of the resulting powders should be low. Hancock et al., *Pharm. Res.* 11(4): 471-477 (1994). However the correlation between water content and stability does not seem to be linear. Chang et al. obtained optimal stabilization of a lyophilized IgG at intermediate water contents of 2-3%. Chang et al., *Journal of Pharm. Sci* 94(7): 1427-1444 (2005).

As a result of this knowledge, the powder resulting from the spray drying process should show low residual moisture and also be protected from humidity during storage. Maa et al., *Pharm. Res.* 15(5): 768-775 (1998). The first can, to a certain extent, be influenced by the process conditions (inlet air temperature ($T_{in}$), relative humidity (RH) of the inlet air); the latter is a matter of leak-proof vials or controllable storage conditions.

III. Formulations of the Invention

Any suitable protein, peptide, antibody, or antigen binding portion thereof, can be employed in preparing the compositions of the present invention. For example, it may be IgG type. Exemplary antibodies, or antigen binding portions thereof, include, but are not limited to, MAK 195F, Adalimumab, or ABT-325. Anti-TNF antibodies suitable for the use according to the invention are well known (for example, as described in EP-A-0 260 610, EP-A-0 351 789, EP-A-0 218 868). Both polyclonal and monoclonal antibodies can be used. Furthermore, TNF-binding antibody fragments such as Fab or F(ab')$_2$ fragments or single-chain Fv fragments are also suitable. A suitable monoclonal anti-hTNF-alpha antibody is described in EP-A-0 260 610, designated AM-195 or MAK-195, which is produced by a hybridoma cell line deposited with the ECACC under the accession number 87 050803. Murine anti-TNF antibody fragment (F(ab')$_2$) also designated MAK 195F (INN: Afelimomab) is also suitable.

In one embodiment, the formulation of the invention comprises an antibody, or antigen-binding portion thereof, which binds human TNFα, including, for example, adalimumab (also referred to as Humira or D2E7; Abbott Laboratories). In one embodiment, the antibody, or antigen-binding fragment thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. Examples and methods for making human neutralizing antibodies that have a high affinity for human TNFα, including sequences of the antibodies, are described in U.S. Pat. No. 6,090,382, incorporated by reference herein.

In one embodiment, the formulation of the invention comprises an antibody, or antigen-binding portion thereof, which binds human interleukin-12 (IL-12), including, for example, the antibody ABT-874 (Abbott Laboratories) (U.S. Pat. No. 6,914,128). ABT-874 is a fully human monoclonal antibody designed to target and neutralize interleukin-12 and interleukin-23. In one embodiment, the antibody, or antigen-binding fragment thereof, has one or more of the following characteristics: it dissociates from human IL-1α with a $K_D$ of $3 \times 10^{-7}$ M or less; dissociates from human IL-1β with a $K_D$ of $5 \times 10^{-5}$ M or less; and does not bind mouse IL-1α or mouse IL-1β. Examples and methods for making human, neutralizing antibodies which have a high affinity for human IL-12, including sequences of the antibody, are described in U.S. Pat. No. 6,914,128, incorporated by reference herein.

In one embodiment, the formulation of the invention comprises an antibody, or antigen-binding portion thereof, which binds human IL-18, including, for example, the antibody ABT-325 (Abbott Laboratories) (see U.S. Patent Application No. 2005/0147610).

In one embodiment, the formulation of the invention comprises an antibody, or antigen-binding portion thereof, which binds human IL-12, such as the antibody ABT-147 (Abbott Laboratories) (see WO 2007/005608 A2, published Jan. 11, 2007).

In one embodiment, the formulation of the invention comprises an antibody, or antigen-binding portion thereof, which binds human IL-13, such as the antibody ABT-308 (Abbott Laboratories) (see. PCT/US2007/19660).

Examples of proteins that may be included in the powdered formulation include antibodies, or antigen-binding fragments thereof. Examples of different types of antibodies, or antigen-binding fragments thereof, that may be used in the invention include, but are not limited to, a chimeric antibody, a human antibody, a humanized antibody, and a domain antibody (dAb). In one embodiment, the antibody used in the methods and compositions of the invention is an anti-TNFα antibody, or antigen-binding portion thereof, or an anti-IL-12 antibody, or an anti-IL-13 antibody, or antigen binding portion thereof. Additional examples of an antibody, or antigen-binding fragment thereof, that may be used in the invention include, but are not limited to, ABT-147 (Abbott Laboratories), ABT-325 (anti-IL-18; Abbott Laboratories), ABT-308 (Abbott Laboratories), ABT-874 (anti-IL-12; Abbott Laboratories), Afelimomab (Fab 2 anti-TNF; Abbott Laboratories), Humira (adalimumab; Abbott Laboratories), Campath (Alemtuzumab), CEA-Scan Arcitumomab (fab fragment), Erbitux (Cetuximab), Herceptin (Trastuzumab), Myoscint (Imciromab Pentetate), ProstaScint (Capromab Pendetide), Remicade (Infliximab), ReoPro (Abciximab), Rituxan (Rituximab), Simulect (Basiliximab), Synagis (Palivizumab), Verluma (Nofetumomab), Xolair (Omalizumab), Zenapax (Daclizumab), Zevalin (Ibritumomab Tiuxetan), Orthoclone OKT3 (Muromonab-CD3), Panorex (Edrecolomab), and Mylotarg (Gemtuzamab ozogamicin).

In one alternative, the protein is a fusion protein, including, but not limited to, Pulmozyme (Dornase alfa), Rebif, Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept) Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa).

Other examples of proteins that may be included in the methods and compositions described herein, include mammalian proteins, including recombinant proteins thereof, such as, e.g., growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGFα and TGF-β, including TGF-β 1, TGF-β 2, TGF-β 3, TGF-β 4, or TGF-β 5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); a growth and differentiation factor, an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

Polyclonal Antibodies

Polyclonal antibodies generally refer to a mixture of antibodies that are specific to a certain antigen, but bind to different epitopes on the antigen. Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized (e.g., keyhole limpet hemocyanin, serum albumin, bovine thyroglobulin, or soybean trypsin inhibitor), using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1NCNR$, where R and $R_1$ are different alkyl groups. Methods for making polyclonal antibodies are known in the art, and are described, for example, in *Antibodies: A Laboratory Manual*, Lane and Harlow (1988), incorporated by reference herein.

Monoclonal Antibodies

A "monoclonal antibody" as used herein is intended to refer to a hybridoma-derived antibody (e.g., an antibody secreted by a hybridoma prepared by hybridoma technology, such as the standard Kohler and Milstein hybridoma methodology). For example, the monoclonal antibodies may be made using the hybridoma method first described by Kohler et al., Nature, 256:495 (1975), or may be made by recombinant DNA methods (U.S. Pat. No. 4,816,567). Thus, a hybridoma-derived dual-specificity antibody of the invention is still referred to as a monoclonal antibody although it has antigenic specificity for more than a single antigen.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991), which describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Antibodies and antibody fragments may also be isolated from yeast and other eukaryotic cells with the use of expression libraries, as described in U.S. Pat. Nos. 6,423, 538; 6,696,251; 6,699,658; 6,300,065; 6,399,763; and 6,114, 147. Eukaryotic cells may be engineered to express library proteins, including from combinatorial antibody libraries, for display on the cell surface, allowing for selection of particular cells containing library clones for antibodies with affinity to select target molecules. After recovery from an isolated cell, the library clone coding for the antibody of interest can be expressed at high levels from a suitable mammalian cell line.

Additional methods for developing antibodies of interest include cell-free screening using nucleic acid display technology, as described in U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315. These methods can be used to transcribe a protein in vitro from a nucleic acid in such a way that the protein is physically associated or bound to the nucleic acid from which it originated. By selecting for an expressed protein with a target molecule, the nucleic acid that codes for the protein is also selected. In one variation on cell-free screening techniques, antibody sequences isolated from immune system cells can be isolated and partially randomized polymerase chain reaction mutagenesis techniques can be used to increase antibody diversity. These partially randomized antibody genes are then expressed in a cell-free system, with concurrent physical association created between the nucleic acid and antibody.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Humanized Antibodies

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting non-human (e.g., rodent) CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some framework (FR) residues are substituted by residues from analogous sites in rodent antibodies. Additional references which describe the humanization process include Sims et al., J. Immunol., 151:2296 (1993); Chothia et al., J. Mol. Biol., 196:901 (1987); Carter et al., Proc. Natl. Acad. Sci. USA, 89:4285 (1992); Presta et al., J. Immunol., 151:2623 (1993), each of which is incorporated by reference herein.

Human Antibodies

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 (1991)).

Bispecific Antibodies

Bispecific antibodies (BsAbs) are antibodies that have binding specificities for at least two different epitopes. Such antibodies can be derived from full length antibodies or antibody fragments (e.g., F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences.

The fusion preferably is with an immunoglobulin heavy chain constant domain, comprising at least part of the hinge, $C_{H2}$, and $C_{H3}$ regions. It is preferred to have the first heavy-chain constant region ($C_{H1}$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment, the human neutralizing, antibody, or an antigen-binding portion thereof, having a high affinity for human TNFα is an isolated human antibody, or an antigen-binding portion thereof, with a light chain variable region (LCVR) having a CDR3 domain comprising the amino acid sequence of SEQ ID NO:3, or modified from SEQ ID NO:3 by a single alanine substitution at position 1, 4, 5, 7 or 8, and with a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11. Preferably, the LCVR further has a CDR2 domain comprising the amino acid sequence of SEQ ID NO:5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO:7 (i.e., the D2E7 VL CDR1) and the HCVR has a CDR1 domain comprising the amino acid sequence of SEQ ID NO:8 (i.e., the D2E7 VH CDR1).

In another embodiment, the human neutralizing, antibody, or an antigen-binding portion thereof, having a high affinity for human TNFα is an isolated human antibody, or an antigen-binding portion thereof, with a light chain variable region (LCVR) comprising the amino acid sequence of SEQ ID NO:1 (i.e., the D2E7 VL) and a heavy chain variable region (HCVR) comprising the amino acid sequence of SEQ ID NO:2 (i.e., the D2E7 VH). In certain embodiments, the antibody comprises a heavy chain constant region, such as an IgG 1, IgG2, IgG3, IgG4, IgA, IgE, IgM or IgD constant region. Preferably, the heavy chain constant region is an IgG 1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., Methods in Enzymology, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments that are not necessarily bispecific. For example, Fab' fragments recovered from *E. coli* can be chemically coupled in vitro to form bivalent antibodies. See, Shalaby et al., J. Exp. Med., 175:217-225 (1992).

Various techniques for making and isolating bivalent antibody fragments directly from recombinant cell culture have also been described. For example, bivalent heterodimers have been produced using leucine zippers. Kostelny et al., J. Immunol., 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. USA, 90:6444-6448 (1993) has provided an alternative mechanism for making bispecific/bivalent antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by using single-chain Fv (sFv) dimers has also been reported. See Gruber et al., J. Immunol., 152:5368 (1994).

In one embodiment, the formulation of the invention comprises an antibody that is bispecific for IL-1 (including IL-1α and IL-1β). Examples and methods for making bispecific IL-1 antibodies can be found in WO 08/082,651, published Jul. 10, 2008.

Dual Variable Domain (DVD) Binding Proteins

Dual variable domain (DVD) binding proteins are proteins that include two or more antigen binding sites, and are tetravalent or multivalent binding proteins. DVDs may be monospecific, i.e., capable of binding one antigen or multispecific, i.e., capable of binding two or more antigens. DVD binding proteins comprising two heavy chain DVD polypeptides and two light chain DVD polypeptides are referred to as a DVD Ig™. Each half of a DVD Ig comprises a heavy chain DVD polypeptide, and a light chain DVD polypeptide, and two antigen binding sites. Each binding site comprises a heavy chain variable domain and a light chain variable domain with a total of six CDRs involved in antigen binding per antigen binding site. In certain embodiments, the DVD can include any of the DVDs disclosed in US Patent Publication No. 20070071675 to Wu et al., published Mar. 29, 2007, which is incorporated herein by reference.

DVD-Igs are useful as therapeutic agents to simultaneously block two different targets to enhance efficacy/safety and/or increase patient coverage. Such targets may include soluble targets (IL-13 and TNF) and cell surface receptor targets (VEGFR and EGFR). It can also be used to induce redirected cytotoxicity between tumor cells and T cells (Her2 and CD3) for cancer therapy, or between autoreactive cell and effector cells for autoimmune/transplantation, or between any target cell and effector cell to eliminate disease-causing cells in any given disease.

In addition, DVD-Ig can be used to trigger receptor clustering and activation when it is designed to target two different epitopes on the same receptor. This may have benefit in making agonistic and antagonistic anti-GPCR therapeutics. In this case, DVD-Ig can be used to target two different epitopes on one cell for clustering/signaling (two cell surface molecules) or signaling (on one molecule). Similarly, a DVD-Ig molecule can be designed to trigger CTLA-4 ligation, and a negative signal by targeting two different epitopes (or 2 copies of the same epitope) of CTLA4 extracellular domain, leading to down regulation of the immune response. Similarly, DVD-Ig can target two different members of a cell surface receptor complex (e.g., IL-12R alpha and beta). Furthermore, DVD-Ig can target CR1 and a soluble protein/pathogen to drive rapid clearance of the target soluble protein/pathogen.

Additionally, DVD-Igs of the invention can be employed for tissue-specific delivery (target a tissue marker and a disease mediator for enhanced local PK thus higher efficacy and/or lower toxicity), including intracellular delivery (targeting an internalizing receptor and a intracellular molecule), delivering to inside the brain (targeting transferrin receptor and a CNS disease mediator for crossing the blood-brain barrier). DVD-Ig can also serve as a carrier protein to deliver an antigen to a specific location via binding to a non-neutralizing epitope of that antigen and also to increase the half-life of the antigen.

The invention provides stable powdered compositions including any suitable protein, including those described herein, and prepared as described herein. For example, the powder can include a protein or peptide (e.g., an antibody, or an antigen binding portion thereof), and an excipient, wherein the composition includes less than about 6% residual moisture. In certain embodiments, the composition includes less than about 5.5%, 5%, 4.4%, 4%, 3.5%, or 3% residual moisture. In some embodiments, the composition includes less than 2% or 1% residual moisture. In other embodiments, the composition includes a residual moisture range bounded by the above values, e.g., between about 4% and 6%, between about 4.5% and 5.5%, or between about 3% and 5% residual moisture. In some embodiments the residual moisture content of the resulting powdered composition is between about 1% and about 3%, between about 1.5% and 2.5%, between about 1.4% and about 2%, between about 4% and 6%, or between about 4.5% and about 5%. In other embodiments the powdered composition includes about 1%, 1.5%, 2%, 2.5%, 3%, 3.5%, 4%, 4.5%, 5%, 5.5%, 6%, 6.5%, or 7% residual moisture.

In some embodiments, the protein retains its biological activity for a desired period of time. In one embodiment, the powder is stable at ambient temperatures and humidity for at least 3 months. In some embodiments, the powder is stable for at least 6 months, 9 months, 1 year, 2 years, 3 years or 5 years at ambient temperatures and humidity. In other embodiments, the powder is stable at 40° C. for at least 3 months. In additional embodiments, the powder is stable at 40° C. for at least 3 months, 6 months, 9 months, 1 year, 2 years or 5 years. In still additional embodiments, the powder is stable at 40° C. and ambient humidity for at least 3 months, 6 months, 9 months, 1 year, 2 years or 5 years.

The powdered compositions of the invention and/or pharmaceutical compositions including the powdered compositions can include an excipient. Suitable excipients include, but are not limited to, trehalose, sucrose, sorbitol, polyethylene glycol, at least one amino acid, histidine, alanine, arginine, glycine, or a mixture thereof. The method can further include adding an acidic component, an antioxidant, and/or a tonicity modifier.

In some embodiments, the composition has a mass ratio of excipient to antibody, or antigen binding portion thereof, of about 0.27:1.0 to about 2.8:1.0, about 0.27:1.0 to about 1.4:1.0, about 0.27:1.0 to about 0.7:1.0, or about 0.7:1, and the excipient is trehalose or sucrose. In other embodiments, the composition has a mass ratio of excipient to antibody, or antigen binding portion thereof, of about 0.27:1.0 to about 2.8:1.0, about 0.27:1.0 to about 1.4:1.0, about 0.27:1.0 to about 0.7:1.0, about 0.7:1, or about 0.35:1, and the excipient is sorbitol.

Additionally, the present invention provides pharmaceutical preparations that include an effective amount of the powders described herein. The pharmaceutically acceptable carrier can be any carrier acceptable for parental, oral, enteral, or topical administration. The carrier can be solid, semi-solid or liquid (e.g., water or an organic liquid) or combinations thereof.

The powder can be mixed (e.g., dissolved or embedded) in a pharmaceutically acceptable carrier. The pharmaceutically acceptable carrier may be, e.g., acceptable for parental administration, and may include, e.g., water. The method can further including adding one or more acidic components, antioxidants, and/or tonicity modifiers to the pharmaceutical composition. Additionally or alternatively, suitable additives can be added to the pharmaceutical compositions of the invention, e.g., buffers, viscosity modifiers, flavorants, colorants, etc.

Powdered pharmaceutical compositions can be melt extruded, pressed or otherwise processed to form, e.g., tablets or other solid or semi-solid compositions. The powder can be coated with, e.g., polymers such as PLGA to form sustained release and/or delayed release pharmaceutical compositions. Additionally or alternatively compositions may be encapsulated or coated with, e.g., an enteric coating. Coatings and/or excipients can be employed, e.g., to protect the drug against precipitation, denaturation or oxidation by organic solvents such as polyethylene glycol, (e.g., PEG 400), ethanol, DMSO, NMP, glacial acetic acid, or the like.

Liquid compositions, e.g., aqueous compositions are also contemplated. Such compositions can be suitable, e.g., for oral or intravenous administration, and can include any suitable excipient or additive such as a tonicity modifier or buffers. In some embodiments, the liquid pharmaceutical composition has a low percentage of protein aggregates, despite the high concentration of the aqueous protein formulation. In one embodiment, the aqueous composition includes water and a high concentration of a protein, e.g., antibodies, which contains less than about 5% protein aggregates, even in the absence of a surfactant or other type of excipient. In one embodiment, the composition includes no more than about 7.3% aggregate protein; the composition includes no more than about 5% aggregate protein; the composition includes no more than about 4% aggregate protein; the composition includes no more than about 3% aggregate protein; the composition includes no more than about 2% aggregate protein; or the composition includes no more than about 1% aggregate protein. In one embodiment, the composition includes at least about 92%, at least about 93%, at least about 94%, at least about 95%, at least about 96%, at least about 97%, at least about 98%, or at least about 99% monomer protein. Ranges intermediate to the above recited concentrations, e.g., at least about 98.6% monomer protein, no more than about 4.2% aggregate protein, are also intended to be part of this invention. In addition, ranges of values using a combination of any of the above recited values as upper and/or lower limits are intended to be included.

IV. Uses of the Invention

The compositions of the invention may be used both therapeutically, i.e., in vivo, or as reagents for in vitro or in situ purposes. As described and exemplified herein, spray drying may be used to prepare dry protein powders for use as starting material for the development/manufacturing of, for example: (a) an enteral formulation of ABT-874 for treatment of Ulcerative Colitis, (b) a topical formulation of adalimumab for diabetic ulcers; and (c) a pulmonary dosage form of ABT-308 for treatment of asthma. In addition, the spray dried antibodies may be used with a MELTREX melt extrusion process, since it could be possible that the monoclonal antibody (mAb) incorporated within the glassy excipients matrix (e.g., trehalose) exhibit a higher stability towards thermal unfolding/denaturation. This might offer again opportunities for the development of new solid protein dosage forms, e.g., for the oral administration of proteins.

Therapeutic Uses

The methods of the invention may also be used to prepare pharmaceutical compositions having characteristics that are advantageous for therapeutic use. The pharmaceutical compositions, including liquid or solid compositions, may be used as a pharmaceutical composition or formulation to treat a disorder in a subject.

The compositions of the invention may be used to treat any disorder for which the therapeutic protein, peptide, antibody, or antigen binding portion thereof, is appropriate for treating. A "disorder" is any condition that would benefit from treatment with the antibody. This includes chronic and acute disorders or diseases including those pathological conditions that predispose the mammal to the disorder in question. In the case of an anti-TNFα antibody, a therapeutically effective amount of the antibody may be administered to treat an autoimmune disease, such as rheumatoid arthritis, an intestinal disorder, such as Crohn's disease, a spondyloarthropathy, such as ankylosing spondylitis, or a skin disorder, such as psoriasis. In the case of an anti-IL-12 antibody, a therapeutically effective amount of the antibody may be administered to treat a neurological disorder, such as multiple sclerosis, or a skin disorder, such as psoriasis. Other examples of disorders in which the compositions of the invention may be used to treat include cancer, including breast cancer, leukemia, lymphoma, and colon cancer.

The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

The term "treatment" refers to both therapeutic treatment and prophylactic or preventative measures. Those in need of treatment include those already with the disorder, as well as those in which the disorder is to be prevented.

The aqueous or solid compositions may be administered to a mammal, including a human, in need of treatment in accordance with known methods of administration. Examples of methods of administration include intravenous administration, such as a bolus or by continuous infusion over a period of time, intramuscular, intraperitoneal, intracerebrospinal, subcutaneous, intra-articular, intrasynovial, intrathecal, intradermal, transdermal, oral, topical, or inhalation administration.

In one embodiment, the composition is administered to the mammal by subcutaneous administration. For such purposes, the composition may be injected using a syringe, as well as other devices including injection devices (e.g., the Inject-eas and Genject devices); injector pens (such as the GenPen); needleless devices (e.g., MediJector and BioJector); and subcutaneous patch delivery systems.

Also included in the invention are delivery devices that house the composition. Examples of such devices include, but are not limited to, a syringe, a pen, an implant, and a patch. An example of an autoinjection pen is described in U.S. application Ser. No. 11/824,516, filed Jun. 29, 2007.

The appropriate dosage ("therapeutically effective amount") of the protein, peptide, antibody or antigen binding portion thereof, will depend, for example, on the condition to be treated, the severity and course of the condition, whether it is administered for preventive or therapeutic purposes, previous therapy, the patient's clinical history and response to the protein, the type of protein used, and the discretion of the attending physician. The compositions of the invention are suitably administered to the patient at one time or over a series of treatments and may be administered to the patient at any time from diagnosis onwards. The compositions may be administered as the sole treatment or in conjunction with other drugs or therapies useful in treating the condition in question.

In one embodiment, the compositions of the present invention, e.g., those including afelimomab and/or any other suitable antibody or antigen binding portion thereof, are employed therapeutically. In one embodiment, the compositions are pharmaceutical compositions for use in treating sepsis.

Sepsis, Tumor Necrosis Factor-α (TNF-α) and Afelimomab

Sepsis is defined as a systemic inflammatory response to an infection. The infection may be viral, bacterial, fungal or parasitic, for example. Sepsis eventually leads to an activation of immunocompetent cells and a systemic inflammatory response associated with the release of multiple cytokines (TNF-α, IL-1, etc.). There are different stages/kinds of sepsis, as defined by the ACCP (American College of Chest Physicians): SIRS (Systemic Inflammatory Response Syndrome) (systemic inflammatory response of various genesis (infection, erythema, etc.); sepsis (SIRS caused by an infection); severe sepsis (sepsis with organ mal-/dysfunction); and septic shock (sepsis with shock)). To diagnose these kinds of sepsis different criteria must be met.

The primary occurring immune response is orchestrated and amplified by a variety of secondary mediators. The organism is not in a position to limit the inflammation to the place of its origin (mostly the lung or the blood circulation). Different organs can be affected, which has a strong impact on several bodily functions. Therefore possible signs of sepsis include hyperthermia, tachypnea, tachycardia, hypotension and confusion. Because of the variety of indicators, sepsis is very difficult to diagnose, a contributing factor to the high mortality rate in sepsis patients.

Different medications to treat septic patients are known, among them drotrecogin α (activated protein C) and antithrombin III to block blood coagulation and cortisone (in low doses) to attenuate the inflammation. Bloos et al., *Aktuelle Ernährungsmedizin,* 28:186-190 (2003). As TNF-α is one of the main mediators of sepsis, one approach to handle sepsis is to block TNF-α to avoid its effects. Local release of TNF-α increases blood flow and vascular permeability. That allows influx into the infected tissue of fluids, cells and proteins that participate in host defense. To prevent spread of the infection to the blood, small vessels later clot, and the fluid drains to lymph nodes where the adaptive immune response is initiated. During systemic infections TNF-α works in a similar way, leading to shock and disseminated intravascular coagulation. The results are a depletion of clotting factors, constant bleeding and multiple organ failure. Janeway et al., Immunobiology (Garland Publishing, 1994). Blocking TNF-α can be achieved by parenteral administration of an anti-TNF-α-antibody. By designing the antibody fragment afelimomab, a better tissue penetration combined with lower immunogenic problems should be achieved.

In some embodiments, the invention includes administering to a subject (e.g., a human), a protein, peptide, antibody or antigen binding protein thereof, such that the activity of its target or targets in the subject is inhibited and treatment is achieved. In some embodiments, the disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune hemolytic anemia, Coombs positive hemolytic anemia, acquired pernicious anemia, juvenile pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, hemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic arteriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, hashimoto's thyroiditis, hay fever, heart transplant rejection, hemochromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia—reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, mycobacterium avium intracellulare, mycobacterium tuberculosis, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranuclear Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, Subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangiitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, and xenograft rejection of any organ or tissue.

Non-Therapeutic Uses

The compositions of the invention may also be employed for non-therapeutic uses, i.e., in vitro purposes. For example, protein powders and related compositions described herein may be used for diagnostic or experimental methods in medicine and biotechnology, including, but not limited to, use in genomics, proteomics, bioinformatics, cell culture, plant biology, and cell biology. For example, the compositions described herein may be used to provide a protein needed as a molecular probe in a labeling and detecting method. An additional use for the compositions described herein is to provide supplements for cell culture reagents, including cell growth and protein production for manufacturing purposes.

Compositions containing high concentrations of, e.g., antibodies, may be used as a reagent for laboratory use. Such highly concentrated forms of an antibody would expand the current limits of laboratory experiments.

Another alternative use for the formulation of the invention is to provide additives to food products. In some embodiments, because the compositions of the invention consist essentially of protein and sugar, they may be used to deliver high concentrations of a desired protein, such as a nutritional supplement, to a food item. The compositions of the invention can thus provide a high concentration of the protein.

Articles of Manufacture

In another embodiment of the invention, an article of manufacture is provided that contains a protein powder or related composition of the present invention, and provides instructions for its use. In an embodiment, the article of manufacture comprises a container. Suitable containers include, for example, one or more bottles, vials (e.g., dual chamber vials), syringes (including single and dual chamber syringes), autoinjector pens containing a syringe, and test tubes. The container may be formed from a variety of materials such as glass, plastic or polycarbonate. The container holds the aqueous formulation and the label on, or associated with, the container may indicate directions for use. For example, the label may indicate that the composition is useful or intended for subcutaneous administration. The label may, e.g., direct the user to add a liquid, e.g., sterile water or saline to prepare the composition for administration, e.g., by injection. The container holding the composition may be a multi-use vial that allows for repeat administrations (e.g., from 2-6 administrations) of, e.g., an aqueous formulation. The article of manufacture may further comprise a second container. The article of manufacture may further include other materials desirable from a commercial and user standpoint, including other buffers, diluents, filters, needles, syringes, and package inserts with instructions for use.

This invention is further illustrated by the following examples, which should not be construed as limiting.

EXEMPLIFICATION OF THE INVENTION

In this example, a Fab fragment of an IgG molecule was spray-dried and analyzed. The scope of this study was to find suitable formulations and process conditions for spray drying the Fab fragment with a high yield and good storage stability, as it is intended for use as a storage intermediate. Stabilization of the protein during the spray drying process and the subsequent storage was achieved by the addition of different sugars. For this study trehalose, sucrose and sorbitol were added to the liquid protein concentrate. Protein stability was analyzed using data from various analytical methods, among them size exclusion chromatography, dynamic light scattering, turbidity measurements and isoelectric focusing.

Materials

MAK 195 F Concentrate

The protein used in this example was afelimomab (MAK 195 F) provided by Abbott Laboratories as an aqueous solution containing: MAK 195 F (12.4 mg/mL); NaCl (8.77 mg/mL); $Na_3PO_4$ (1.64 mg/mL); Pluronic® F68 (0.1 mg/mL); and water (q.s.). The MAK 195 F concentrate had a pH of 7.2 and was close to isotonic (~286 mosmol/kg). It had a viscosity of 0.981 mPas (measured with a Schott Ubbelohde viscosimeter) and a density of 1.0086 g/cm³ (measured with a DMA 46 from Chempro).

The afelimomab protein is an $F(ab')_2$ fragment of a murine anti-TNF-alpha antibody ($IgG_3$) with an approximate molecular weight of 100 kilodalton (kDa). It is produced by pepsin cleavage of the $IgG_3$ monoclonal antibody resulting in light chains comprising 214 amino acids each, and heavy chains containing 233-241 amino acids. Approximately 30% of the Fd' fragments are glycosylated at $Ser_{H222}$. Because of different glycosylation patterns, afelimomab has up to seven isoforms in an isoelectric point (IEP) range of 7.5 to 8.8.

The concentrate was obtained under dry ice in portions of about 400 g. To avoid repeated freeze-thaw-cycles and long term storage in the liquid state the concentrate was thawed and aliquoted in 40-50 mL portions, stored at −80° C. and freshly thawed before usage.

Excipients

Three different sugars were used to stabilize the protein: D-Sorbitol (Sigma, Product: S-7547, Lot: 108H01461); Sucrose (Sigma, Product S-7903, Lot 014K0010); and D-(+) Trehalose dihydrate (Sigma, Product: T5251, Lot: 113K3775).

All aqueous solutions were prepared with double-distilled water (Fi-stream 4BD; Fisons) and, if necessary, filtered through a 0.2 μm membrane filter (Schleicher & Schuell).

Methods

Spray Drying

Spray drying experiments were performed on a Büchi Mini-Spray Dryer B-191 (FIG. 1) using the high-performance cyclone 1 for powder recovery. The drying air was filtered through a Luwa Ultrafilter 2 (fiber glass; filterclass: HEPA H13 High Efficiency Particle Absorber) at an airflow rate of 800 l/min (90% aspirator power) prior to entering the heating device 3 and the drying chamber. All liquid feeds were filtered through a 0.22 µm filter unit before being transported to the drying chamber 4 by a peristaltic pump 5 ($Q_{LF}$=~3 mL/min; silicon tube Ø=3 mm). Atomization was performed by a two fluid nozzle 6 (orifice diameter: 0.7 mm) using compressed air from the in-house supply ($Q_{AA}$=700 l/h). The two fluid nozzle was equipped with an automatic cleaning system, also using compressed air (4.5 bar) and a water-cooling system. After spray drying the resulting powders were recovered from the collecting vessel 7 in a dry air glove box (RH<2%), filled in glass vials (chlorobutyl rubber stoppers), sealed with parafilm and stored at −80° C. The powder yield was defined as the amount of powder inside the collecting vessel divided by the total solids in the liquid feed. Powder depositions on the inside of the cyclone were not collected.

Size Exclusion Chromatography (SEC)

Size exclusion chromatography was used to detect soluble aggregates. A Tricorn Superose 12/300 GL column (separation range 1-300 kDa) purchased by Amersham Biosciences was connected to a Perkin Elmer High Pressure Liquid Chromatography (HPLC) system, comprising a series 200 LC pump, an ISS 200 autosampler and a 235C diode array detector. Prior to the Superose column a phenomenex security guard pre-column (loaded with AJ0-4489 cartridges) was installed to avoid contamination with coarse particles. The mobile phase (buffer A, flow rate: 0.5 mL/min) was a potassium phosphate buffer (pH 6.9) with addition of sodium chloride (0.5 mol/l), filtered through a 0.2 µm membrane filter (Schleicher&Schuell, FP 30/0.2 CA) and degassed for about 10 minutes using helium. All samples were measured directly (e.g., liquid feed) or redissolved carefully with buffer A to a protein concentration of 1 mg/mL (spray dried (sd) powders) and analyzed shortly after preparation. The injection volume per run was 100 µl, and generally all samples were measured twice (liquid feed) or thrice (sd powders) to ensure reproducible results. All chromatograms were integrated manually using the Perkin Elmer TotalChrom Navigator software, version 6.2.

Differential Scanning Calorimetry (DSC)

Thermal events were investigated using a Mettler Toledo DSC 822$^e$. 5-15 mg powder was weighed out (Mettler, AT DeltaRange®) into aluminum pans under dry-air conditions (glove box). The aluminum pans were cold-sealed and inserted into the calorimeter, where they were exposed to a defined temperature program (depending on the formulation) of heating and cooling in turn through the expected Tg (heating/cooling rate: 10° C./min). The glass transition temperature was estimated by Mettler STARe Software V 6.10, preliminarily defined as the midpoint of the endothermic transition during the heating step. Only the second and the third heating cycles were taken into account, to avoid interference of other irreversible endothermic events. Throughout the experiment the measurement cell was dried and purged with $N_2$ gas.

Wide-Angle X-Ray Diffraction (WAXD)

Crystallinity of the powders was investigated by x-ray powder diffraction using a Philips model X'pert MPD with Cu $K_\alpha$ radiation (λ=0.15418 mm) at 40 kV/40 mA and 25° C. Powder amounts of 60-80 mg were filled into the aluminum sample holder and scanned immediately. All scans were measured in the range 2θ=0.5°–40° with a step size of 0.02°/s. Sample crystallinity (degree of crystallinity) was calculated from the crystalline and amorphous areas of the diffraction diagram (see below) by using a method based on that of Black and Lovering. Black, Lovering *Journal of Pharmacy and Pharmacology* 29:684-687 (1977).

$$C=I_c/(I_c+I_a)=AUC_{crystalline}/AUC_{total}=(AUC_{Total}-AUC_{amorphous})/AUC_{Total}$$

C is the degree of crystallinity (sometimes also described as percent crystallinity, when multiplied by 100), $I_c$ and $I_a$ represent the intensities of the X-rays scattered by the crystalline or amorphous regions, which equals the area under the curve (AUC) of the peaks and the broad halos, respectively. $AUC_{amorphous}$ was calculated by cutting the crystalline peaks out of the diagram and using curve fitting.

Dynamic Light Scattering

The dynamic light scattering (DLS) measurements were performed with a Zetasizer Nano ZS (Malvern, Germany, software: DTS version: 4.2) to detect soluble as well as insoluble aggregates. The Zetasizer uses a laser light of 633 nm and detects scattering at 173° (back scatter detection). It has a measurement range of 0.6-6000 nm for size measurements. Particle size was determined by measuring the Brownian motion of the particles in the sample. Malvern Instruments: Zetasizer Nano Series User Manual. MAN 0317, Issue 2.0, March 2004. Liquid formulations were tested without any additives, and powders were diluted with double-distilled water (filtered through 0.2 µm) to the original protein concentration. By using low volume cuvettes (disposable low volume cuvettes, Malvern) only 0.5 mL solution was needed per measurement. Tests with 2 mL cuvettes provided the same results (data not shown). After 2 minutes of equilibration time (25° C.) 3 measurements of each sample were performed with 5 runs each (run duration: 30 s, delay between runs: 2 s). This procedure was conducted three times for every powder/solution sample. The resulting diagrams were exported as score tables and converted into diagrams via MS Excel leading to three plotted curves per sample showing size-volume and size-intensity distributions.

Scanning Electron Microscopy (SEM)

Particle size and morphology were examined via electron microscopy pictures using an Amray 1810 T Scanning Electron Microscope at 20 kV. Small powder samples were fixed on Al sample stubs (G301, Plano) using self-adhesive films. After being sputtered with Au at 20 mA/kV (Hummer JR Technics) for 1.5 minutes the samples were placed under the microscope and pictures of different magnifications (normally 1000×, 2000× and 3000×) were taken. Generally, the pictures taken at a magnification of 3000× were evaluated.

Karl Fischer Titration

Moisture content of the spray dried (sd) powders was measured with a Mitsubishi Moisture Meter (CA-06 Coulometric) and a Mitsubishi water vaporizer (VA-06). Powder samples of approximately 70 mg were filled into a special sample holder under dry-air conditions (glove box). The empty sample holder was weighed with a Mettler AT DeltaRange analytical balance. By connecting the sample holder to the vaporizer unit, the powder was filled into a glass boat being pulled into the heated oven unit. While the water was being vaporized (150° C.) and transferred quantitatively into the titration cell via a nitrogen gas stream (~200 mL/min), the sample holder was reweighed to calculate the real sample weight. Titration started at a titration rate of ≤0.01 µg H$_2$O/min.

Sub-Visible Particles

Particle contamination, e.g., of the redissolved sd powders was observed with the computer-aided particle counting device Syringe (Klotz, Germany, Software: SW-CA Version 1.2). The liquid was sucked through a flow-through cell that was reduced to a diameter of 250 µm in front of a laser. When particles were hit by the laser beam, their detected intensity was reduced. The attenuation of the laser light was an indicator of particle size. All powders were reconstituted to their original concentration with double-distilled water (filtered through 0.2 µm) and 0.8 mL solutions were pumped through the system (once for flushing the system, three times for the particle calculations). Results were calculated for 1 mL of solution. For pharmaceutical applications the software graded particles in 8 different size ranges (1-50 µm) according to the regulations of the United States Pharmacopoeia (USP) or the European Pharmacopoeia (Ph. Eur.).

Isoelectric Focussing (IEF)

The IEF separation of afelimomab was based on the charge differences of the Fd' fragment and light chain variants. It primarily served as an identity test for afelimomab, but it could also be used as an instrument for stability tests. The focusing was performed with a Pharmacia Multiphor II chamber attached to a Serva Blue Power 3000 power supply. Ready-to-use gels with a pH gradient of 6-9 (Servalyt Pr ecotes 6-9, 125×125 mm, thickness 0.3 mm; Serva, Germany) were placed on the cooling plate (4° C., covered with some Bayol F as heat transfer medium). All samples were diluted to a protein concentration of about 4 mg/mL, 10 µL were placed on the gel. The focusing program started at 200 V and took about 195 min (end-point voltage 2000 V). After fixation for 20 minutes the gels were stained with Coomassie Brilliant Blue (20 min) and then destained several times. The solutions used are listed in Table 1, below.

TABLE 1

| Solution Name | Composition | Amount | |
|---|---|---|---|
| Fixative Solution | Trichloroacetic Acid | 40 | g |
| | Ethanol 96% | 100 | mL |
| | Double-Distilled Water | 100 | mL |
| Staining Solution | Coomassie Brilliant Blue R250 | 400 | mg |
| | Acetic Acid | 40 | mL |
| | Ethanol 96% | 160 | mL |
| | Double Distilled Water | ad 400 | mL |
| Destaining Solution | Acetic Acid | 50 | mL |
| | Ethanol 96% | 250 | mL |
| | Double Distilled Water | ad 500 | mL |

After rinsing with water and drying overnight at room temperature the gels were inspected and scanned using a Desaga CAB UVIS VD 40 workstation with ProViDoc® Software (Version 3.20).

Turbidity

Turbidity is an expression of the optical property that causes light to be scattered and absorbed rather than transmitted in straight lines through a sample. It can be caused by any suspended particles, including solids, colloids and gas bubbles. As turbidity is not a well-defined parameter, it was measured by comparing the samples with opalescence standards, e.g., hydrazine gels. A Hach Ratio XR turbidimeter was used to estimate the nephelometric turbidity units (NTU) of the samples. The turbidimeter was calibrated with Hydrazine standards. After measuring a blank-value of the Nessler-tubes, the samples were diluted or reconstituted with double-distilled water (filtered through 0.2 µm) to the original protein concentration and then placed in the beam of light. To exclude the influence of glass inhomogeneity it was important to mark the direction of the tubes during the blank measurement and to use the tube in the same direction for the sample measurement.

Coloration

To detect changes in the coloration of the redissolved sd powders, a LICO 400 (Hach Lange, Switzerland) was used, which is a calorimeter for color measurement of transparent liquids. It determined the reference solution closest to the sample and quantified the color variation between sample and reference. In this study the CIE-Lab color space, defining colors as coordinates of brightness (L, black-white) and color (±a, red-green; ±b, yellow-blue), was used (CIE is the abbreviation for Commission Internationale d'Eclairage). The LICO 400 was calibrated using the standard solutions from the Ph. Eur. (BG 5-7, brownish-yellow, diluted; B 5-9, brown). All powder samples were reconstituted to the original concentration, 200 µl was filled into a small volume quartz glass cuvette.

UV-Spectroscopy

To determine the protein concentration of the concentrate or ultrafiltrated aliquots, a Perkin Elmer Lambda 25 UV/VIS Spectrometer was used. The samples were diluted to a protein concentration of approximately 0.6 mg/mL. Three quartz glass cuvettes were filled with the sample solution and each one of them was measured thrice at wavelength (λ)=280 nm and λ=320 nm. The absorbance values (given by the UV WinLab 5.0 software, Perkin Elmer) were used to calculate the protein concentration, using the following equations:

$$c=[(A_{280}-A_{320})_{mean}/1.37]*F(\text{mg/mL})$$

$$1.37=\epsilon_{280\ nm}-\epsilon_{320\ nm}$$

$$F=V_{H2O}/V_{prot}+1$$

In these equations, F is the dilution factor, A represents the measured absorbance, ε is the molar extinction coefficient (absorbance of a 1 mg/mL solution, using a 1 cm cuvette), and V stands for the volume in the first dilution step.

Cross Flow Filtration

To achieve higher concentrated afelimomab solutions, the concentrate was ultrafiltrated using a Millipore Labscale® TFF system. The original afelimomab concentrate was permanently pumped along a filter device with a molecular weight cut off (MWCO) of 30 kDa. All ingredients except the protein passed through the membrane and were collected in an external vessel. The protein itself was returned to the circular flow. The current concentration could roughly be estimated by a volume scale. The exact protein concentration was calculated after the filtration process was stopped by using UV-spectroscopy.

Results

Characterization of the MAK Concentrate

The freshly thawed concentrate normally showed aggregation of about 0.9-1% (differences between the aliquots are possible, so every aliquot is examined via SEC right after thawing) and no detectable fragmentation. According to experiments with a molecular weight marker kit (carbonic anhydrase, molecular weight ($M_r$)=29 kDa and β-amylase, $M_r$=200 kDa), the aggregates were mainly dimers. The DLS diagrams showed that the monomer has a hydrodynamic diameter of about 10 nm. The concentrate exhibited relatively low sub-visible particle contamination and turbidity values of approximately 5 NTU. The typical IEF band pattern of the 5 isoforms was seen. In all further IEF experiments, the pure concentrate was used as a marker/standard, so any differences were detected directly.

In the coloration measurements, the concentrate was closest to the standard solution B9, which was a nearly colorless solution with a slight touch of brown. The concentrate had a density of 1.009 g/cm$^3$ and a viscosity of 0.981 mPas (both measured at 20° C.).

Spray Drying of the MAK Concentrate

The first spray drying experiments were made with the pure concentrate that was free from any additional stabilizers. The degree of protein damage during the drying process was determined.

Process Stability of MAK

To determine how the protein suffers during the spray drying process, the process parameters for the first experiments were adopted from existing studies on the Büchi 191, e.g. Maury: $T_{in}$=130° C., $Q_{LF}$=~3 mL/min, $Q_{AA}$=700 l/h, $Q_{DA}$=800 l/min, resulting in a $T_{out}$ of approximately 80° C. Maury et al., *Eur. Journal of Pharm. and Biopharm.* 59(3): 565-573 (2005).

The resulting white powder (cyclone yield: ~60%) comprised spherical, donut-shaped or indented particles with a diameter up to 13 μm. The redissolved powder (22.9 mg powder/mL water) had a protein concentration of 12-13 mg/mL, suggesting that the loss of powder was caused by the process of spray drying and the separation performance of the cyclone. No preferential loss of protein or excipient from protein solutions could be detected because of their amorphous state after spray drying. The X-ray diffraction diagram of the sd MAK concentrate showed crystalline peaks, caused by the other components of the bulk drug substance (e.g. sodium phosphate and sodium chloride). The peak pattern was very close to that of sd sodium chloride. The residual moisture content of the powder was 1.4-2%, being dependent on the ambient conditions during the process (RH of the drying air, room temperature, etc.).

In the SEC, the redissolved powder showed a distinct increase in aggregation (2.5-3%). This was, however, not much for a protein solution without stabilizers. Maury found up to 17% for a spray dried, dialyzed IgG solution. Maury et al., *Eur. Journal of Pharm. and Biopharm.* 59(2):251-261 (2005). This indicates that fragments are less sensitive during spray drying than full-length antibodies, although this is not so for freeze-thaw-induced aggregation. Wang et al., *Journal of Pharm. Sci.* 96(1):1-26 (2007). Another possibility is that there was a stabilizing effect caused by the presence of sodium chloride. Arakawa et al. experienced stabilizing interactions between proteins and sodium chloride in solutions; however they only investigated higher salt concentrations than those used here. Arakawa et al., *Biochemistry* 21:6545-6551 (1982). The increase in aggregation was also seen in the DLS and IEF results.

During the isoelectric focusing, a new band appeared at the starting point of the focusing. It could have been attributed to large aggregates that could not penetrate into the gel and therefore could not move according to their isoelectric point (according to Serva GmbH the pores of their IEF gels have a cut-off of about 200-300 kDa). The DLS results showed an additional peak at μm-size. The peak was hard to see in the size-volume distribution, but was clear in the size-intensity distribution. Few large particles scatter much more light than many small particles do, because the intensity of scattering of a particle is proportional to the sixth power of its diameter. Malvern Instruments: Zetasizer Nano Series User Manual. MAN 0317, Issue 2.0, March 2004. The additional peak was apparently caused by the protein, because the DLS experiments with a placebo concentrate did not show a peak of that hydrodynamic diameter. As these large aggregates were not seen in the SEC they must be insoluble. Particle contamination of the redissolved powder was increased throughout all particle fractions. However, the process on the laboratory spray drier could not completely exclude particle contamination (although the inlet drying air was filtered). Furthermore, opening the vial for taking samples could also have been a particle source. Moreover turbidity of the redissolved powder was significantly increased compared to the concentrate (concentrate: 5 NTU; concentrate sd: 118 NTU).

Finding a Suitable $T_{in}$

To find out whether a $T_{in}$ of 130° C. is suitable for spray drying the afelimomab protein, an experimental series with different temperatures was conducted. The $T_{in}$ and resulting $T_{out}$ at $Q_{LF}$=~3 mL/min for this series are listed in Table 2. The intention was to find a satisfactory compromise between drying efficiency and protein process stability.

TABLE 2

| $T_{in}$ (° C.) | Approx. $T_{out}$ (° C.) |
|---|---|
| 100 | 61 |
| 130 | 80 |
| 155 | 95 |
| 180 | 108 |

No differences in particle morphology were observed, except that the 180° C. particles were a little more wrinkled than the 100° C. ones, but the differences were very slight. The water content tended to decrease with increasing $T_{in}$ with a substantial downwards step between 100° C. and 130° C. There were no substantial differences in aggregation detectable, so aggregation did not seem to be very temperature dependent. The powder yield showed a small improvement at higher temperatures. All these results recommended use of a high $T_{in}$, but the isoelectric focusing (IEF) and dynamic light scattering (DLS) results indicated that the appropriate $T_{in}$ for afelimomab was in the mid range. The intensity of the aggregation band in the IEF was linearly dependent on the drying air inlet temperature. Also, the DLS diagrams showed inferior results at 180° C. The monomer peak showed up at a higher hydrodynamic diameter (about 16 nm). The aggregates not only seemed to become more numerous, as assumed in the IEF, but also larger. Moreover, the monomer peak was shifted in shape (towards a smaller distribution) and size, indicating substantial damage to the protein. Particle contamination was higher at 180° C. as well, especially in the small particle fractions (<15 μm). According to these results only 130° C. and 155° C. can be considered as acceptable for further investigations. As the results for these two inlet temperatures are similar, a $T_{in}$ of 130° C. was chosen. Operating at this temperature should minimize the thermal stress on the protein, while providing overall acceptable results for the product quality.

Sources of Aggregation

The spray drying process comprises a number of sources of inactivation for proteins. Some can be reduced by modifying the formulation with excipients, whereas other sources of inactivation cannot be influenced. The increase in aggregation during the process cannot be clearly attributed to a single stress factor. Heat stress is controllable to a certain extent by choosing the right $T_{in}$, here about 130° C. To find out the degree of inevitable stresses, the following experiments were performed.

Influence of the Peristaltic Pump

To quantify the influence of shear stress of the peristaltic pump on aggregation, SEC was used. Ten mL of the afelimomab concentrate was used as a liquid feed. The sample was pumped through the tubing and the peristaltic pump of the Büchi B-191 and collected just before entering the two fluid nozzle. The liquid feed was tested before and after the pumping process. No change in aggregation was noticed. It can be assumed that the peristaltic pump of the laboratory spray dryer does not influence or increase aggregation of the afelimomab protein. Pump induced insulin aggregation, observed by Brennan et al. (*Diabetes* 34, 353-359 (1985)), only occurred when insulin came out of solution after long term pumping. As the passage through the tubing in this study takes at most only a few minutes, the danger of damage is very small.

Influence of the Atomization Process

The extent of shear stress during atomization was tested by atomizing two samples of concentrate (2 mL) and testing via SEC and IEF afterwards. In the IEF, no differences could be observed between the samples (no additional band or changes in the band pattern). The SEC results showed a slight increase in aggregation. This increase was not as high as it was during the whole spray drying process. It can therefore be concluded that a small part of aggregation was caused by atomization, but as Maa et al. assumed, protein damage may be the result not only of shear forces, but rather of the large air/liquid interface. Maa et al., *Biotechnology and Bioengineering* 54(6):503-512 (1997).

Influence of Thermal Stress

Proteins are heat sensitive material, but not every protein is equally sensitive to thermal stress. To determine how much the afelimomab concentrate can bear up against temperature (thermal stress), small amounts of protein solution were exposed to different temperatures over different time periods. Criteria for the stability of the concentrate were SEC-data, IEF results and the optical appearance of the solution. After the appearance of coagulation, the trials were terminated. The results are shown in Table 3, below.

TABLE 3

|  | 1 hour | 4 hours | 24 hours |
|---|---|---|---|
| 40° C. | clear | clear | clear |
| 45° C. | clear | clear | slightly turbid |
| 50° C. | clear | slightly turbid | turbid |
| 55° C. | slightly turbid | turbid | coagulation |
| 60° C. | turbid | coagulation |  |
| 65° C. | coagulation |  |  |
| 80° C. | coagulation |  |  |

The concentrate could not withstand temperatures higher than about 60° C. In the IEF gels the occurrence of turbidity was accompanied by the appearance of an additional band at the starting point. Bleaching of the original band pattern indicates a loss of soluble protein. A loss of soluble protein was also detected in the SEC-files. The monomer peak shrank with increasing temperature and time (ordinate scaling). 40° C. did not influence the afelimomab concentrate, even when applied over 24 hours. Thermal stress damage of the protein was not represented by an increase of aggregation, but by the appearance of fragments. The aggregation peak remained largely unchanged. Heat stress applied to the concentrate, therefore, resulted in fragmentation and coagulation, whereas heat stress applied to the atomized concentrate during sd resulted mainly in aggregation. The afelimomab concentrate could withstand temperatures of up to about 50° C. for short time periods. At about 60° C. protein damage happened quickly. During the spray drying process the droplets were exposed to wet bulb temperature ($T_{wb}$), which is normally 25-30° C. below $T_{out}$ (in this study normally 80° C.), and the time of exposure was very short. Mumenthaler et al., *Pharm. Res.* 11(1):12-20 (1994).

Summary

Aggregation was not thought to be caused by shear forces during the pumping procedure. Atomization was responsible for parts of the aggregation increase during the spray drying process. Thermal stress played a major role for protein stability, but when applied to the concentrate, it resulted in fragmentation and insoluble aggregates. As the droplet reached the critical temperature of about 55° C. during sd (25-30° C. below $T_{out}$, postulated by Mumenthaler et al., but only for a very short period), the aggregation increase seemed to be caused by the interplay of temperature and atomization. Mumenthaler 1994.

Spray Drying Experiments with Excipients

To optimize the stabilization of the afelimomab protein, different excipients were tested. The goal was sufficient stability during the drying process and subsequent storage.

Addition of 10-150 mM Sorbitol

Figure 2:
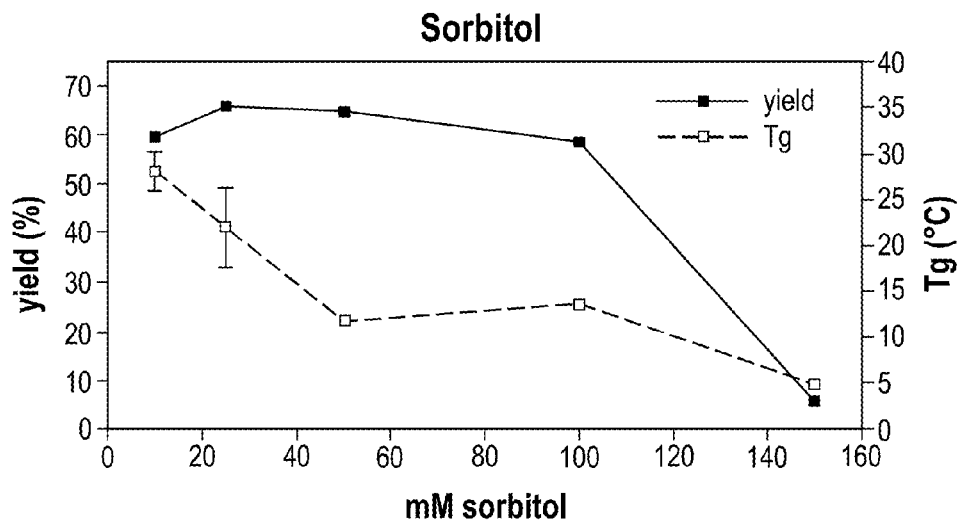
FIG. 2 depicts the yield and Tg of different sorbitol-MAK mixtures.
Figure 3:
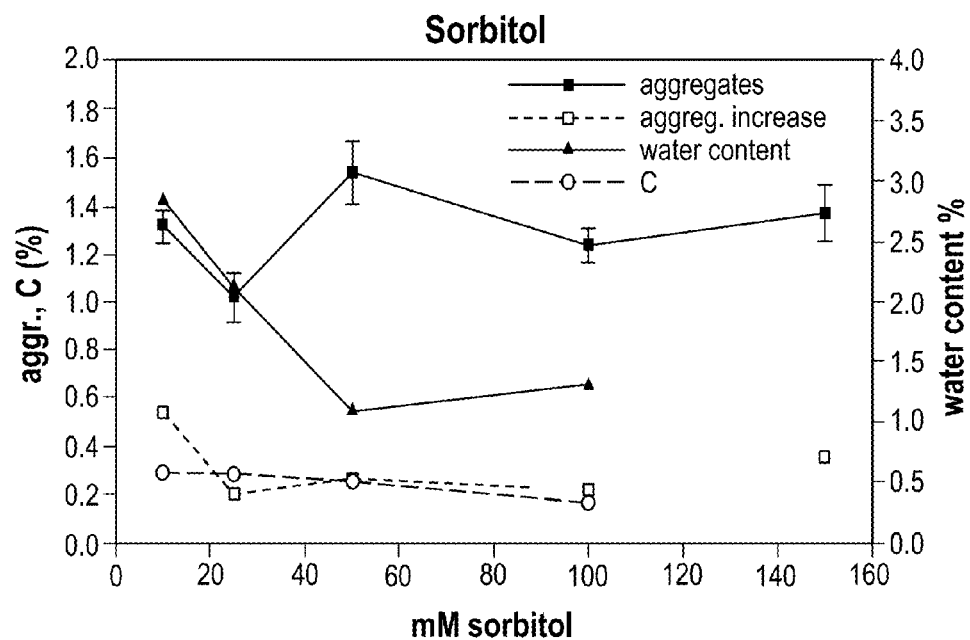
FIG. 3 depicts aggregation, crystallinity and water content of different sorbitol-MAK mixtures.

In the current example, 10, 25, 50, 100 or 150 mM sorbitol was added to the afelimomab concentrate to determine the best molar ratio of stabilizer to protein as shown in Table 4. The results are shown in FIGS. 2 and 3. For the 150 mM sorbitol solution, the $T_g$ drops down far beyond process, and even room-temperature and it is not possible to spray dry this mixture properly, as seen in the very low yield. The mixture cannot be dried during its passage through the drying chamber, and it is still sticky when entering the cyclone separator, so a large part adheres to the cyclone wall and cannot be collected. Maury et al., *Eur. Journal of Pharm. and Biopharm.* 59(3):565-573 (2005).

TABLE 4

| mM | $m_{excipient}$ (mg) | $V_{concentrate}$ | Mass Ratio excipient:MAK |
|---|---|---|---|
| 10 | 27 | 15 | 0.14:1 |
| 25 | 67 | 15 | 0.35:1 |
| 50 | 135 | 15 | 0.7:1 |
| 100 | 270 | 15 | 1.4:1 |
| 150 | 410 | 15 | 2.1:1 |

Figure 4:
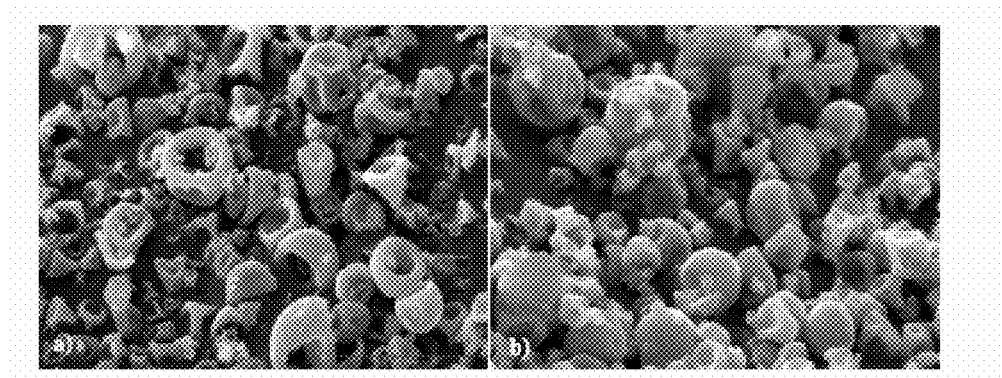
FIG. 4 provides scanning electron microscopy (SEM) images of sorbitol-MAK mixtures 3000× (a) 25 mM (b) 100 mM.

Due to the small yield, Karl-Fischer titration (KF) and wide-angle x-ray diffraction (WAXD) analysis of these samples could not be performed. The increase in aggregation was not much dependent on the amount of sorbitol, except that 10 mM was insufficient. Different amounts of sorbitol did not influence particle morphology; although the more excipient present in the mixture, the more the particles adopted a round shape (see FIG. 4). Although it was not possible to spray dry a pure sorbitol solution (as a contrast), the placebo powders of the different sorbitol concentrations all showed spherical particles.

The degree of crystallinity decreased with higher sorbitol net weight. The IEF results largely conformed to the results of the pure concentrate in that an additional band can only be detected vaguely, if at all. The 10 mM mixture also showed an unexpected DLS diagram. The clear peaks at micrometer size were hardly detectable in the size-volume distribution, so the amount of large aggregates was very low. However, 25, 50 and 100 mM of added sorbitol showed almost identical diagrams. Particle contamination seemed to be linearly dependent on the amount of sorbitol (solids), showing the largest step between 10 mM and 25 mM. The differences were, however, mainly limited to the smaller particle sizes. The values for particles larger than 15 µm were more or less equal. Adequate stabilization of the afelimomab concentrate seemed thus to be feasible with the addition of 25 or 50 mM sorbitol. These two mixtures did not show great differences, except the water content and, as a consequence, the resulting $T_g$.

Addition of 10-100 mM Trehalose

Figure 5:
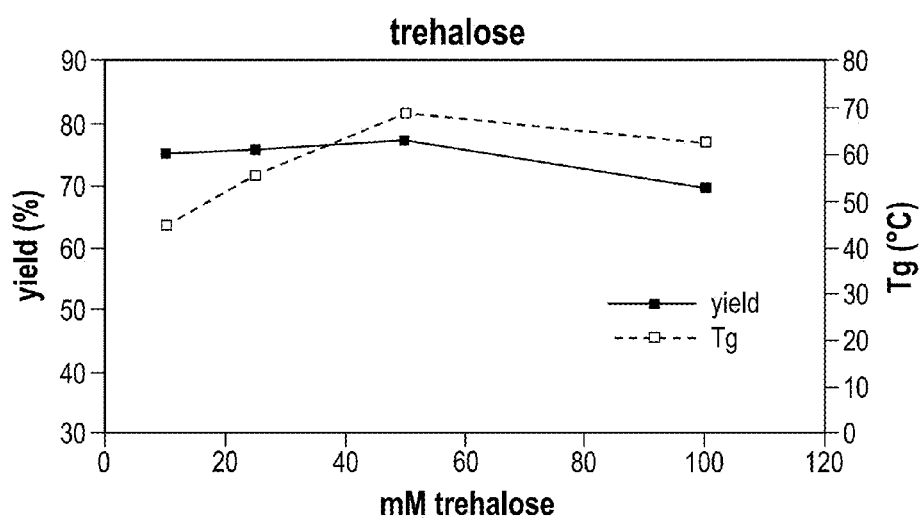
FIG. 5 depicts yield and Tg of different trehalose-MAK mixtures.
Figure 6:
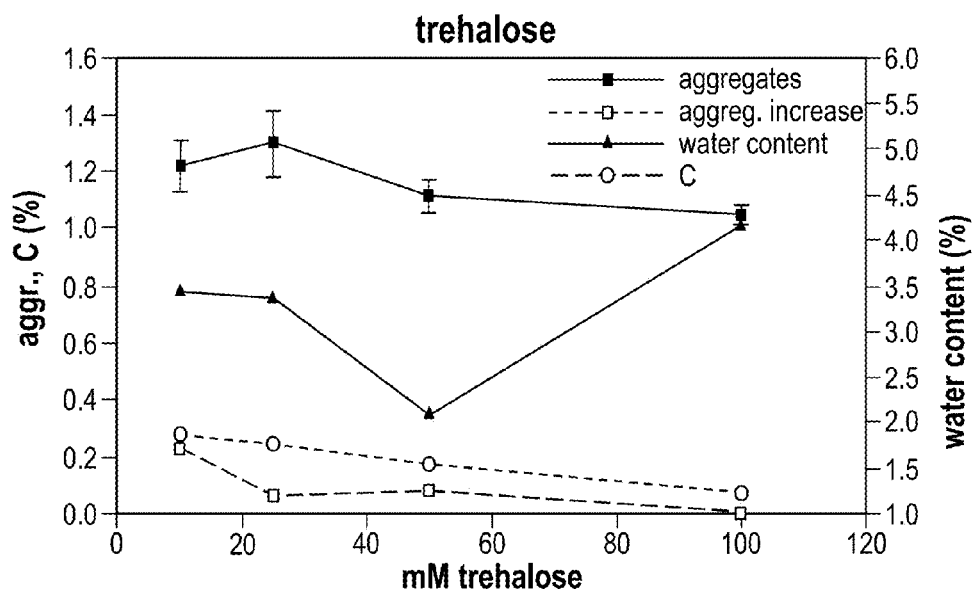
FIG. 6 depicts aggregation, crystallinity and water content of different trehalose-MAK mixtures.

Because of the results found with high sorbitol amount, the trehalose test series excluded the 150 mM mixture. Trehalose was added as trehalose dihydrate, so the mixtures comprised between 56.7 and 567 mg trehalose dihydrate in 15 mL afelimomab concentrate, the mass ratios of trehalose:MAK can be seen in Table 5. As seen in FIGS. 5 and 6, the results were similar between 25 mM and 100 mM. The yield averaged a little higher overall concentrations, compared to sorbitol. With trehalose a very good stabilization was obtained, and also the yields were stable over all concentrations. Increased aggregation was minimal, and only for the 10 mM mixture a small increase in aggregation in the SEC was seen (0.2%).

TABLE 5

| mM | $m_{excipient}$ (mg) | $V_{concentrate}$ | Mass Ratio excipient:MAK |
|---|---|---|---|
| 10 | 51 | 15 | 0.27:1 |
| 25 | 128 | 15 | 0.7:1 |
| 50 | 255 | 15 | 1.3:1 |
| 100 | 510 | 15 | 2.7:1 |

Figure 7:
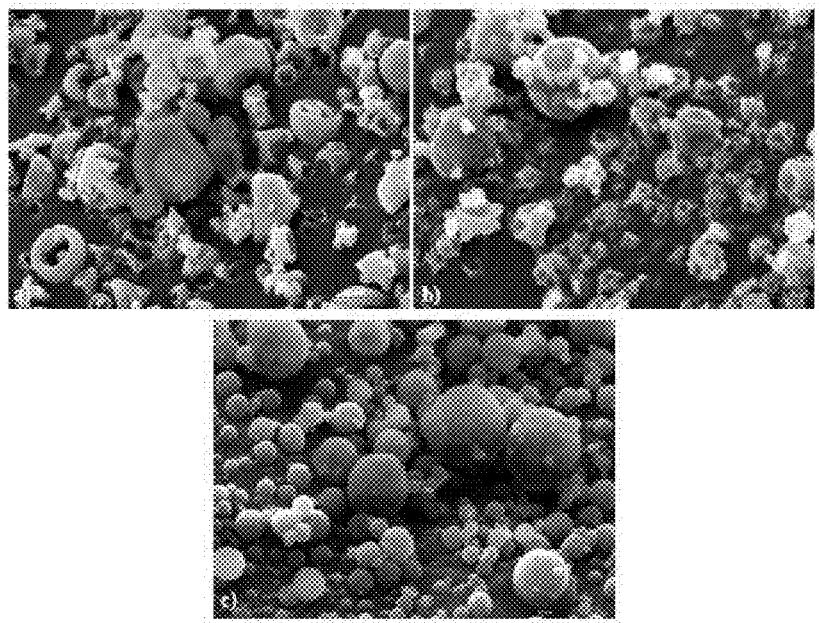
FIG. 7 provides SEM images of trehalose mixtures (3000×) (a) 10 mM trehalose; (b) 100 mM trehalose, and (c) pure trehalose spray dried.
Figure 8:
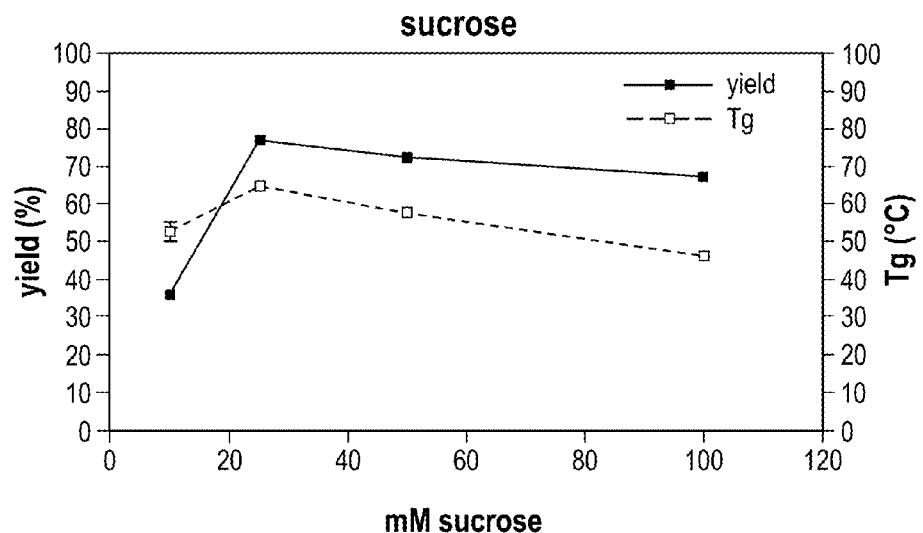
FIG. 8 depicts yield and Tg of different sucrose-MAK mixtures.
Figure 9:
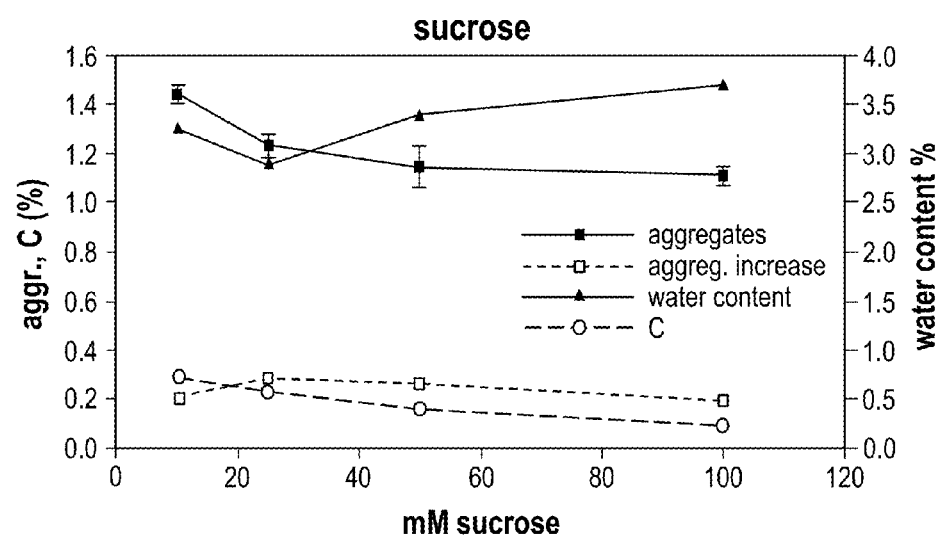
FIG. 9 depicts aggregation, crystallinity and water content of different sucrose-MAK mixtures.

Nevertheless, insoluble aggregation occurred in all mixtures, as seen in the DLS diagrams. The amount of monomer was comparable to the sorbitol results. The crystallinity and sphericity of the particles varied directly with the amount of trehalose. Addition of trehalose caused the particles to adopt a rounder shape, as spray drying of pure trehalose provides spherical particles (see FIG. 7). As seen in the sorbitol experiments, particle contamination seemed to be affected by the excipient concentration, but it was again limited to the small particle sizes (≤15 µm). Because of the high $T_g$ of trehalose (the $T_g$ for dried trehalose is 115° C.), the $T_g$ of the trehalose mixtures is also high, which could be an advantage for powder stability studies. Adler et al., *Journal of Pharm. Sci.* 88(2):199-208 (1999). 25 mM and 50 mM seemed to be the most promising proportions of trehalose to produce powders with appropriate process and storage stability. The resulting powders showed less residual water than the sorbitol powders did. Because of the satisfying results with these mixtures, the option of a subsequent test with 150 mM trehalose was abandoned.

Addition of 10-100 mM Sucrose

Additions of 25 mM to 100 mM sucrose to the afelimomab concentrate were tested (see Table 6). From 25 mM to 100 mM the addition of sucrose provided high powder yields of 70 to 80% (FIGS. 8 and 9). The $T_g$ reached an optimum at 25 mM. Aggregation increase did not differ substantially throughout all of the concentrations. Again the degree of crystallinity (C) decreased linearly with the amount of sucrose. The residual water content of the different powders averaged slightly higher than that observed for trehalose mixtures. Sphericity of the particles was influenced by the amount of sucrose. The protein tended to form indented spheres, whereas sucrose tended to form spherical particles.

TABLE 6

| mM | $m_{excipient}$ (mg) | $V_{concentrate}$ | Mass Ratio excipient:MAK |
|---|---|---|---|
| 10 | 51 | 15 | 0.27:1 |
| 25 | 128 | 15 | 0.7:1 |
| 50 | 255 | 15 | 1.3:1 |
| 100 | 510 | 15 | 2.7:1 |

In the DLS-files, the amount of monomer was lower with 100 mM sucrose compared to 10 mM, but this impression was limited to the intensity-size distribution diagrams. In the volume-size distribution for 100 mM sucrose, the aggregation peak was hard to detect. In the 10 mM mixture larger aggregates could be seen (>1 μm). These additional peaks did not show up in the remainder of the sucrose mixtures. The IEF gels did not show any substantial irregularities. An additional band was only vaguely detectable for 50 and 100 mM, and the original band pattern of the concentrate could clearly be seen. Particle contamination decreased from 10 mM to 100 mM, showing the largest step between 10 mM and 25 mM. With larger particle size, the differences became smaller, so for particles larger than 15 μm all mixtures showed similar particle amounts. Taking all these results into account, the addition of 10 mM sucrose to the afelimomab concentrate was insufficient; the best results were obtained with 25 mM and 50 mM.

Summary

Comparing the results for the three excipients in different amounts it is evident that 10 mM of excipient is not sufficient to provide protein conservation during the spray drying process. The most favorable results for all excipients were thus obtained with 25 mM and 50 mM; 100 mM or even 150 mM did not improve the results (for 150 mM sorbitol quite the contrary). The results for aggregation increase were a little higher for sorbitol; the remainder of the results (sucrose and trehalose) were broadly similar. Trehalose and sucrose protected the afelimomab protein to the same extent and were superior to sorbitol.

Storage Stability Studies

The spray dried powders were exposed to different temperature and residual humidity conditions for 3 months. The test conditions were: a refrigerator (5° C., no humidity); 25° C. at 60% relative humidity (similar to Central Europe, North America); and 40° C. at 75% relative humidity (similar to Southeast Asia).

Preparation and Inspection Plan

The pure concentrate as well as a spray-dried placebo was stored. The placebo powders comprised the same solids as the verum powders (spray dried protein-excipient mixtures), except for the afelimomab protein. The powder amounts needed for the analytical tests were calculated beforehand to estimate the batch size of the liquid feed. Three or four batches of 50 mL liquid feed were spray dried under the same conditions; the resulting powders were mixed together as one bulk from which the calculated amounts were filled into small Al-vials with a Viton® sealing fluoroelastomer and a Duroplast®-screw cap. The Al-vials with the Viton® sealing fluoroelastomer were selected, because they showed only small water vapour permeability in preliminary tests (no change in water content of spray dried lactose was observed when stored under 65% RH at room temperature over 10 days). At each examination time (t=1, 2 and 3 months) two identical samples (Al-vials) of each mixture were removed from the different air-conditioned chambers. One was used for analysis; the other was transferred to a freezer and stored at −80° C. (as a reserve for possible additional tests). This gave a total of 152 vials, 48 for removal from the chambers each month (4 verum, 4 verum reserve, 4 placebo, 4 placebo reserve for every temperature) plus 8 vials that were stored at −80° C. without any additional thermal treatment (pure concentrate or freshly spray dried powders).

Afelimomab Concentrate

The SEC results (see Table 7). SEC chromatograms indicated that at 5° C. the concentrate only suffered minor damage by aggregation, but it seems these aggregates were not mainly dimers. The broad plateau of the aggregate peak indicated the presence of trimers/oligomers. Higher temperatures and longer storage periods lead to severe degradation, seen by the occurrence of fragmentation and the decreasing AUC of the chromatogram.

TABLE 7

| Sample | Peak | Peak | Time (min) | Area (%) |
|---|---|---|---|---|
| 5° C. 1 month | 1 | Aggregates | 21.9 | 2.6 |
| | 2 | Monomer | 24.4 | 97.4 |
| 25° C. 2 months | 1 | Aggregates | 21.6 | 3.0 |
| | 2 | Monomer | 24.2 | 87.4 |
| | 3 | Fragments | 27.5 | 9.6 |
| 40° C. 3 months | 1 | Monomer | 24.6 | 7.5 |
| | 2 | Fragments | 27.4 | 92.5 |

The storage stability kinetics of the different fractions were studied. Whereas the amount of monomer constantly fell at all temperatures, aggregation seemed to switch into fragmentation after about 2 months at 25° C. and 40° C. At 40° C. aggregation was no longer detectable as a separate peak in the chromatogram and after 3 months the peak pattern was dominated by the fragmentation peak. The severe damage at 40° C. could already be observed by macroscopically analyzing the sample. After 1 month, the concentrate stored at 40° C. showed turbidity, whereas the 5° C. and 25° C. samples showed only a small shift in coloration, not visible with the naked eye.

Turbidity measurements showed comparable results. Clear shifts in turbidity were only detectable at 40° C. in the verum (sample containing protein) as well as in the placebo concentrate. After 1 month, the concentrate showed a value of over 150 NTU still increasing in the following months. Because of optical turbidity the DLS measurements were terminated for the 40° C. samples. At lower temperatures no changes were detectable. Particle measurements provided additional information about fragmentation and aggregation. The fine particle fraction decreased (particles <25 μm), whereas the number of large particles constantly grew, presumably representing insoluble aggregates not detected by SEC (as assumed by the decreasing AUC of the chromatograms). These should also be the particles responsible for the visible turbidity of the samples.

Until now, damage at 25° C. did not seem very serious. This impression was, however, disproved when analyzing the IEF gels. After 1 month already a small shift in the band intensities could be seen, and after 3 months the band pattern was definitely distinct from the original. The band for the isoform with the highest isoelectric point (IEP) (pH 8.6-8.7) completely disappeared. 40° C. storage caused severe damage after 1 month, becoming even worse during the stability tests.

The afelimomab concentrate was therefore relatively stable when stored at a cool temperature. But as soon as the concentrate was placed at higher temperatures, degradation took place via different pathways. Even room temperature (25° C.) was a stress factor when stored over a long period.

Stability of Spray Dried Powders

To provide long term stabilization via spray drying, the afelimomab concentrate with additional excipients should show degradation no worse than the results for the concentrate stored at 25° C. As an additional test, a Karl Fischer Titration right after the spray drying process, and after 3 months storage, was conducted to examine the seal of the Al-vials (so far only tested for short periods) and/or the influence of moisture on the stability of the spray dried powders.

Concentrate+25 mM Sorbitol

The samples stored at 5° C. and 25° C. show good stability over 3 months (as shown in Table 8). In the SEC results, no clear variations could be found (Δ aggregation is below 1%). At 40° C. substantial degradation took place, aggregation showed a strong increase and large multimers appeared in addition to the dimer peak. After 3 months a clear fragment peak could be detected.

TABLE 8

| Sample | Peak | Peak | Time (min) | Area (%) |
|---|---|---|---|---|
| 25° C. 3 months | 1 | Aggregates | 22.3 | 1.9 |
| | 2 | Monomer | 25.1 | 98.1 |
| 40° C. 1 month | 1 | Aggregates | 21.4 | 8.6 |
| | 2 | Monomer | 24.6 | 91.4 |
| 40° C. 3 months | 1 | Aggregates | 22.1 | 12.4 |
| | 2 | Monomer | 25.0 | 82.4 |
| | 3 | Fragments | 27.2 | 5.2 |

Whereas the samples stored at 5° C. and 25° C. did not show any shift in coloration, the color of the 40° C. sample (redissolved) slightly changed after 1 month and in the course of time even showed visible turbidity. This turbidity was caused by the protein, because the placebo samples did not change coloration at any time or temperature. The most conspicuous results during the turbidity measurements were also obtained at 40° C. Starting at about 20 NTU directly after spray drying, the 40° C. sample reached a value of over 120 NTU after 3 months. However 20 NTU were notedly more than the pure concentrate showed. 40° C. was a critical parameter for the sorbitol mixtures, because it was above $T_g$, so the glassy state could no longer be maintained.

Particle contamination showed similar results. There were only small changes detectable at 5° C. and 25° C. The sample stored at 40° C./75% RH showed a remarkable increase, especially for small particles. This was due to the fact that the powder could not be redissolved without observing a slight turbidity. In the placebo samples the number of particles was much lower than in the verum samples, not limited to special particle sizes. The Al-vials used for storage of the powders did not ensure absolute water vapor impermeability, even though the preliminary studies suggested so.

Karl Fischer Titration was conducted directly after the spray drying process and after 3 months of storage. Water uptake was not protein dependent, because the placebo samples showed equal results, apart from a slightly higher initial value. As the 5° C. powders only showed a small increase in humidity, the water uptake was dependent on the RH of the air-conditioned chambers. The combination of sorbitol and MAK was more hygroscopic than the pure excipient, as the values for the placebo samples were slightly higher than for the verum samples. Temperature, residual humidity and water vapor permeability of the vials did not have any influence on the x-ray-diffraction diagrams. After 3 months there were still no differences in the diffraction pattern compared to the initial diagram (t=0).

Even the macroscopic appearance of the powder was influenced by humidity. Most samples were still flowable bulk material, but the 40° C. samples fused (especially the placebo samples). The increase in aggregation seen in the 40° C. samples was confirmed with the DLS results. While 5° C. and 25° C. still showed the typical pattern (monomer peak at 10 nm and a small aggregation peak at µm-size), a distinct pattern was seen for the 40° C. sample. Even in the size-volume distribution, a small shoulder occurred at the monomer peak, representing a multimer peak that was even more distinct after 3 months. In the IEF gels, changes can be detected after storage at 40° C. for 2 months, an additional band appears at the starting point, not seen at lower temperatures.

Concentrate+25 mM Trehalose

The trehalose mixtures showed good stability (Table 9). During storage at 5° C. and 25° C./60% RH no substantial changes could be detected throughout the whole analytics. Only at 40° C./75% RH did the powders show slightly different results. Aggregation only increased at 40° C. After 3 months, an increase in total aggregation of about 2% was detected. Lower temperatures did not result in significant damage to the protein. But even at 40° C., the amount of monomer after 3 months was still above 95%. With trehalose used as a stabilizer, no formation of fragments was observed, at least there was no distinct peak present in the chromatograms. IgG fragments may be less susceptible to temperature induced aggregation during storage than a complete antibody.

TABLE 9

| Sample | Peak | Peak | Time (min) | Area (%) |
|---|---|---|---|---|
| 25° C. 3 months | 1 | Aggregates | 21.6 | 2.9 |
|  | 2 | Monomer | 24.3 | 97.1 |
| 40° C. 1 month | 1 | Aggregates | 21.4 | 3.3 |
|  | 2 | Monomer | 24.4 | 96.7 |
| 40° C. 3 months | 1 | Aggregates | 21.5 | 4.4 |
|  | 2 | Monomer | 24.3 | 95.6 |

Similar results were obtained during the turbidity measurements. No changes in turbidity could be seen during storage at 5° C. and 25° C., and even the 40° C. sample only showed a small increase in turbidity. The majority of the turbidity was again caused by the protein, since the placebo samples had NTU values close to zero. Particle contamination was not influenced by higher temperatures or higher residual humidity. Apart from the difference between verum and placebo samples, the number of particles largely stayed on the same level over the 3 months of storage. This was also confirmed by the optical appearance of the redissolved powders. All samples lead to a clear solution, and even the coloration measurements did not show any differences during storage.

The Al-vials used for the stability tests could not completely exclude humidity from the powders. The high humidity conditions at 25° C. and 40° C. therefore lead to an increase in humidity of the powders. Powders stored at 5° C. showed unaltered water contents. Both of the stress factors, temperature and increased RH, did not have any influence on the crystallinity of the powder samples. The diffraction diagrams remained unaltered. The sodium chloride peak pattern was still dominating the WAXD diagram. SEC and turbidity measurement results conformed with the results obtained via DLS. Low temperatures and low residual humidity did not harm the protein loaded powders. All samples showed the same pattern, and even the mixture stored at 40° C. did not show extraordinary peaks or peak shoulders. It showed the usual pattern seen with a large peak at about 10 nm and an additional peak at µm-size.

In the IEF results, the only gel showing the additional band at the starting point of the focusing was the one with the 40° C./75% RH samples. Even there, only a slight blue spot was seen (right below "40° C.") after three months. Over all temperatures and humidity conditions, trehalose demonstrated very good stabilization ability for the afelimomab protein.

Concentrate+25 mM Sucrose

Solutions of sucrose in afelimomab concentrate show good storage stability, especially at 5° C. and 25° C./60% RH (Table 10). No alterations in aggregation were observed at these conditions. All chromatograms for 5° C. and 25° C. were similar. Distinct results could only be seen for the 40° C./75% RH samples, where an increase in aggregation of about 2.5% over three months was detected. But still, the amount of monomer at this time was about 95%.

TABLE 10

| Sample | Peak | Peak | Time (min) | Area (%) |
|---|---|---|---|---|
| 25° C. 3 months | 1 | Aggregates | 22.4 | 2.7 |
|  | 2 | Monomer | 24.9 | 97.3 |
| 40° C. 1 month | 1 | Aggregates | 21.6 | 3.0 |
|  | 2 | Monomer | 24.5 | 97.0 |
| 40° C. 3 months | 1 | Aggregates | 22.0 | 5.0 |
|  | 2 | Monomer | 24.9 | 95.0 |

All redissolved powders appeared optically clear and achromatic, not distinguishable from the afelimomab concentrate or the liquid feed. Coloration measurements did not show any alterations in color over the 3 months, even after high temperature storage (40° C.). The solutions were still closest to the reference solutions R6 or B5, which were highly diluted liquids with a touch of red or brown only identifiable with visual aid. With the help of the turbidimeter, no broad alterations were observed. Although there was an increase in turbidity from initially 12 NTU to 20 NTU after storage at 40° C./75% RH, the turbidity results were better than for sorbitol and trehalose, which already showed 20 NTU immediately after spray drying. The placebo samples only showed very low turbidity with no significant changes over the whole stability test period.

Subvisible particle contamination for the verum samples was, as for turbidity, substantially higher than for the placebo samples. In the large particle fractions (particles larger than 10 µm), however, only small alterations were observed. The number of particles larger than 40 µm was normally close to zero, the counts for particles larger than 10 µm were below or around 100 (per mL solution), and so the overall particle contamination was not very high. All degradations at high temperature storage conformed to the results of the Karl Fischer analyses. The higher the residual humidity in the conditioned storage chambers, the higher the amounts of water taken up by the powders. The sucrose samples did not show great differences between verum and placebo powders.

Although the water content increased under higher residual humidity conditions, the absorption of water did not have any influence on the crystallinity of the powders. WAXD diagrams after 3 months showed the same diffraction pattern for all temperatures, identical to the WAXD diagram taken immediately after spray drying (t=0). Only minimal degradation was detected in the DLS diagrams and the IEF gels. After 3 months at 40° C. and 75% RH the sucrose samples showed a light scattering diagram very similar to that immediately after spray drying. The clear monomer peak was at 10 nm hydrodynamic diameter, and a very small peak at μm size (seen in the zoomed section). 40° C. and 75% RH were also the only conditions causing an IEF band pattern distinct from that of the concentrate. A slight band at the starting point of the focusing indicated some large aggregates, but as seen in the DLS diagram, their number was of no substantial importance.

Comparison and Summary

The stability experiments demonstrated that different stabilizing agents lead to different results. Altering excipients or storage conditions did not appear to have an influence on particle morphology. SEM images of an sd sorbitol mixture immediately after spray drying were hardly distinguishable from the trehalose samples stored under 40° C. and 75% RH for 3 months. 5° C. did not lead to severe protein damage; even the afelimomab concentrate did not show substantial degradation over 3 months under these conditions. When stored at 25° C. 60% RH or at 40° C. 75% RH, the pure concentrate responded by showing aggregation and fragmentation.

Trehalose and sucrose showed widely uniform results. The powders had very good stability. Even at 40° C. and 75% RH, only small alterations were detected. Hygroscopicity was, however, one of the parameters showing different results for trehalose and sucrose. Sd powders comprising trehalose overall showed a lower water content after spray drying compared to the sucrose mixtures. As the Al-vials used for the stability tests were not completely impermeable to water vapour, the sucrose powders also had higher water content after 3 months, due to the fact that sd sucrose is more hygroscopic than trehalose.

Another difference between sucrose and trehalose is seen in the turbidity measurements. Sucrose mixtures showed less NTU immediately after spray drying than did the trehalose powders. The turbidity measurements also disclosed another unexpected feature. The spray drying process seemed to be more stressful for the protein-excipient mixtures than storage at elevated temperatures. When spray dried, the powders showed adequate stability at least when stored below the $T_g$ of the sd powder.

Sorbitol also had stabilizing potential. It showed good results at 5° C. and 25° C. The sd powders including sorbitol did not, however, withstand higher temperatures over a long period. A critical parameter for these results seems to be the low $T_g$ of sorbitol. Exceeding this temperature (as seen in the results for 40° C. storage) transformed the glassy formulation into a viscous liquid, enhancing its mobility, opening various degradation pathways.

Attempts to Reduce the Turbidity Increase During the Spray Drying Process

As turbidity was found to be a parameter showing variability during the spray drying process, process parameters were again varied in an attempt to reduce the turbidity values after the drying process to a minimum level. For these experiments process parameters from former drying experiments were used that had already proven to result in minimal damage to the afelimomab protein. To this end, spray drying experiments with 25 mM and 50 mM addition of the excipients trehalose and sucrose were made using a $T_{In}$ of 130° C. and 100° C. As discussed above, a $T_{In}$ of 100° C. showed analytical results close to those obtained with a $T_{In}$ of 130° C. Decreasing $T_{In}$ reduced the thermal stress for the protein and could therefore lead to lower NTU values. Similar considerations applied to the addition of 50 mM and 25 mM excipient. Both formulations showed similar results in previous tests. Increasing the amount of excipient could lead to better NTU values. As both alterations in the process setup did not demonstrate substantial changes in the previous tests, the only analytical method used for these experiments were turbidity measurements.

Addition of Trehalose

Afelimomab concentrate comprising 25 mM and 50 mM trehalose was spray dried at a $T_{In}$ of 100° C. and 130° C. Every formulation was spray dried manifold so that at least 3 sd powders from each experiment could be tested for turbidity. Powder yield did not show substantial differences, neither according to the $T_{In}$, nor to the amount of excipient. The average yield was about 70% showing higher values for 130° C. $T_{In}$ and 25 mM addition of excipient. The results of the turbidity measurements were more varied.

The amount of excipient did not have a great influence on turbidity, as the NTU values for 25 mM and 50 mM trehalose did not differ greatly. Different $T_{In}$, however, lead to distinct turbidity. A $T_{In}$ of 130° C. lead to lower NTU values and standard deviations. At a $T_{In}$ of 100° C. the NTU values in general were higher and also showed greater variability. The values for 130° C. and 25 mM trehalose addition also conformed to the turbidity results obtained during the stability tests.

Addition of Sucrose

Mixtures of afelimomab concentrate with the addition of 25 mM and 50 mM sucrose were spray dried at a $T_{In}$ of 100° C. and 130° C. Different concentrations of sucrose did not seem to have great impact on the powder yield of the spray drying process. All mixtures provided powder yields of about 70%, with the 130° C. powders showing a slightly smaller standard deviation. Even more distinct were the results from the turbidity measurements. NTU values for 25 mM and 50 mM were very close, tending at a $T_{In}$ of 100° C. slightly towards 50 mM sucrose (showing lower turbidity), and to 25 mM addition of sucrose for $T_{In}$=130° C. As these tendencies were not large, the amount of excipient did not have a great impact on the turbidity of the spray dried powders. Much clearer was the decision concerning the $T_{In}$. 100° C. provided substantially higher NTU values, sometimes exceeding 50 NTU, which were not even reached during 3 months of storage at 40° C. for the 130° C. powders. Moreover, the large standard deviation obtained at a $T_{In}$ of 100° C. did not promise reproducible results. When spray dried at a $T_{In}$ of 130° C. the redissolved powders show reproducible low turbidity around 20 NTU. These values also conform the results obtained during the stability tests.

Summary

Turbidity increase during the spray drying process cannot be reduced by decreasing the $T_{In}$. Trehalose containing powders as well as sucrose mixtures showed higher NTU values at 100° C. When using 130° C. as a $T_{In}$, addition of 25 mM excipient provided slightly lower turbidity values than 50 mM. The process parameters concluded from previous experiments (130° C. and 25 mM additive) therefore seem to be optimal for the spray drying of the afelimomab protein. Concerning turbidity, sucrose performed slightly better than trehalose. Powders spray dried from the afelimomab concentrate containing 25 mM sucrose showed an average of 15 NTU, whereas the analogous trehalose mixtures showed an average of 17 NTU.

Spray Drying of More Concentrated MAK 195F Solutions

The afelimomab concentrate comprising 12.4 mg/mL MAK 195F was spray dried successfully in lab scale using trehalose, sucrose or sorbitol, resulting in stable powders.

For scale up drying processes, the process time is a very important factor. Masters, Spray Drying in Practice. SprayDryConsult International ApS; Charlottenlund (2002). To reduce the process time for larger lots, higher protein concentration in the liquid feed enhanced the protein throughput of the spray dryer without substantial impact on the other process parameters. To achieve higher concentrated MAK 195F solutions the afelimomab concentrate was ultrafiltered. During this filtration process water, salts and surfactant were reduced, whereas the protein could not cross the membrane. This lead to an increase in protein concentration, but did not alter the concentration of the other solutes.

Afelimomab Concentrate 50.6 mg/mL

In a first ultrafiltration process, the concentrate reached a concentration of 50.6 mg/mL protein per mL (estimated by using UV-spectroscopy). The solution was optically clear and nearly achromatic (slightly brownish), macroscopically hardly distinguishable from the original afelimomab concentrate (12.4 mg/mL). SEC and DLS did not show alterations from the original concentrate.

The aggregation was still close to the original concentrate (~1%) and the DLS profile exactly matched that of the original concentrate, only showing a single peak at about 10 nm. The protein was not harmed by increasing its concentration. With a higher protein concentration, some measurable physical properties can change. The concentrate 50.6 mg/mL showed a density of 1.017 g/cm$^3$ and a viscosity of 1.375 mPas (both measured at 20° C.), both slightly higher compared to the original concentrate. Also the turbidity values for the concentrate 50.6 mg/mL were higher than for the original solution: 118 NTU and about 5 NTU respectively. This increase was expected, as the amount of macromolecules (protein) in the solution was increased, so there were more macromolecules that could scatter or absorb light to reduce light intensity.

Particle measurements did not show significant changes during the ultrafiltration process. All particle fractions of the concentrate 50.6 mg/mL showed equal or less particle contamination than the concentrate 12.4 mg/mL. Also the IEF gel did not show an additional band. It can be assumed that increasing the concentration of MAK 195F in the solution to 50.6 mg/mL did not lead to substantial damage or other alterations concerning the protein and its functions.

Spray Drying Concentrate 50.6 mg/ml sd without Excipient

The concentrate 50.6 mg/mL was just as susceptible to damage as the concentrate 12.4 mg/mL when spray dried. During the spray drying process aggregation increased to about 2%, an increase of 1%. Powder yield was about 55%, but the water content is relatively high (3.5%). Moreover the powders exhibited some difficulties in handling (filling, etc.) because of their high static charge.

The DLS diagram showed a clear monomer peak and a small shoulder representing small aggregates (oligomers). Contrary to the spray dried original concentrate (12.4 mg/mL), no large aggregates in the form of a peak at μm-size were detected. As there were only small aggregates detectable, no substantial alteration in the IEF gel was seen during the spray drying process.

During the ultrafiltration process the protein concentration was increased, whereas all of the other solutes (NaCl, Na3PO4 and Pluronic® F68) maintained their original concentration. One impact of this alteration can be seen in the X-ray diffraction pattern of the spray dried formulation. Proteins were fully amorphous after spray drying, so the crystalline peaks caused by sodium chloride were substantially downsized. Any influence on particle morphology was not detected except from a tendency towards larger particles, caused by the higher amount of solids in the droplets.

Spray drying the concentrate 50.6 mg/mL without any excipients also lead to a very high particle contamination. Compared to the concentrate 12.4 mg/mL sd all particle fractions below 25 μm contained higher amounts of particles.

By adding excipients prior to spray drying these results should be improvable. As in the stability tests, excipients were added in mass ratios equaling the 25 mM mixtures for the concentrate 12.4 mg/mL.

Addition of Sorbitol

Sorbitol was added in a sorbitol:MAK 195F mass ratio of 0.35:1, according to the 25 mM mixture for the concentrate 12.4 mg/mL. Powder yield of the spray dried mixture was about 60%. The powder had a Tg of 20° C. and a water content of 2.3%. These values widely conformed to the results obtained for the analogous mixtures with the concentrate 12.4 mg/mL (67% powder yield, 2.0% RH, Tg=19° C.). Redissolving the sd powder lead to a clear, nearly achromatic solution, having a coloration closest to reference solution B2 (slightly brownish), just like the initial MAK 195F concentrate 50.6 mg/mL.

After spray drying, the redissolved powder showed a small increase in aggregation. SEC displayed an aggregation level of 1.3%, compared to about 1% for the pure concentrate 50.6 mg/mL. Again, this was no substantial alteration compared to the spray dried concentrate 12.4 mg/mL with 25 mM addition of sorbitol.

The amount of insoluble aggregates was not increased substantially, as seen in the DLS results. A clear monomer peak was detected at a hydrodynamic diameter of 10 nm, as well as an aggregation peak at μm-size. As the solid content of the liquid feed was increased by a factor 2.8, the subvisible particle contamination of the redissolved powder was increased. In particular, the small particle fractions (<10 μm) showed very high contamination levels, whereas the number of large particles (>10 μm) stayed at a level similar to that of the lower concentrated solutions.

Altering protein concentration in the liquid feed had only a small impact on particle morphology. The particles show the typical shape of indented spheres, but there seemed to be a tendency towards larger particles. As the particle diameter for the solutions containing 12.4 mg afelimomab per mL was about 2.5 to 13 μm, spray drying higher concentrated solutions partly lead to particles larger than 15 μm.

Addition of Trehalose

The excipient:MAK 105F ratio of 0.7:1 was adopted from the stability test series, using 25 mM excipient addition for the concentrate 12.4 mg/mL. The amount of excipient was higher in this experiment than in the sorbitol experiment, because trehalose as a disaccharide has a molecular weight about twice as high as sorbitol, a monosaccharide. This increase in solid content of the liquid feed solution made it difficult to obtain the powder yield as high as in former spray drying experiments. Spray drying solutions with a high solid content runs the risk of clogging the powder outlet of the high performance cyclone, and yield decreased below 50% (in this experiment about 45%). The powder was difficult to handle because of high static charge. It had a water content of 3.6% and a Tg of about 66° C., somewhat congruent to the analogous low concentration mixtures (3.3% RH, Tg=56° C.). The redissolved sd powder had a coloration closest to reference solution B2, which was slightly brownish.

The stabilization potential of trehalose was good. An increase in soluble aggregates could not be detected in the SEC chromatogram; aggregation was maintained at a level of 1%, not distinguishable from the original concentrate 50.6 mg/mL. The amount of insoluble aggregates was also very low, as seen in the DLS file, showing the monomer peak and a small amount of large aggregates represented by the peak at μm-size.

Subvisible particle contamination was higher than for the lower concentration mixtures (concentrate 12.4 mg/mL with trehalose). This could be explained by the high solid content, which was about three times as high as in the mixtures using the MAK 195K concentrate 12.4 mg/mL.

Alterations in protein concentration and solid content in the liquid feed did not have great influence on particle morphology. Particle shape did not show any substantial alterations, except the appearance of isolated larger particles in the more concentrated powder.

Addition of Sucrose

To maintain a mass ratio of sucrose:MAK 195F of 0.7:1 (analogous to concentrate 12.4 mg/mL and 25 mM excipient) the amount of sucrose for every spray drying experiment had to be increased by a factor of 4.08 (50.6/12.4). As seen above using this mass ratio, nearly complete protein preservation during the spray drying process was achieved. Spray drying of solutions comprising this high amount of solids runs the risk of clogging the cyclone's powder exit, which has a very small diameter, especially for the high performance cyclone. Therefore powder yield sometimes decreased below 50%, without having any impact on process stability.

As the concentrate 50.6 mg/mL has coloration distinct from the original concentrate 12.4 mg/mL, it is expected that also the redissolved sd powders based on the higher concentrated protein solution showed coloration. The trehalose mixture had coloration closest to reference solution B1, which was slightly brownish.

Aggregation stayed at a level of 1%, not really distinct from the liquid concentrate 50.6 mg/mL or even the original concentrate 12.4 mg/mL.

DLS analysis showed the monomer peak at about 10 nm hydrodynamic diameter, and the well-known small aggregation peak at μm-size representing a small number of large aggregates. The subvisible particle contamination was slightly higher than for the low concentrated mixtures throughout all particle size fractions.

Particle morphology did not differ from the results obtained in the previous experiments comprising the same excipient:MAK 195F ratios. As a consequence of the higher solid content in the liquid feed, some isolated larger particles were seen which were not present in the lower concentrated formulations. Residual moisture of the powder was 2.6%, the Tg of the formulation was about 60° C. Both values were comparable to those obtained for the analogous low concentration formulation in the stability tests (2.6% RH, Tg=63° C.).

Summary

Increasing the protein concentration of the liquid feed to 50.6 mg/mL did not have any substantial impact on the resulting powders. Nearly all of the analytical tests lead to results comparable to the spray drying experiments using the concentrate 12.4 mg/mL with equal mass ratios for excipient:MAK 195F. So the stabilizing potential of the excipients was dependent on the mass ratio excipient:MAK 195F and not on the molar ratio.

As well as in the experiments using the low concentration liquid feed (12.4 mg/mL) trehalose and sucrose lead to nearly identical results concerning process stability during spray drying of afelimomab. The use of sorbitol to stabilize the antibody fragment showed slightly inferior results, especially in aggregation. The IEF comparison of the high concentration powders showed no substantial differences, all mixtures showed the original afelimomab band pattern with no additional bands (large aggregates).

According to the different amounts of excipient there were differences in the WAXD diagrams noticeable. As all sugars used (as well as the protein) were fully amorphous after spray drying, the amount of sodium chloride as the dominating crystalline ingredient controlled the appearance of crystalline peaks. The afelimomab concentrate 12.4 mg/mL had a sodium chloride concentration of 38% w/w (regarding the solids), showing a clear sodium chloride peak at a ° 2 Theta of 32. In the spray dried concentrate, the sodium chloride concentration was about 14% w/w, leading to a decrease in the crystalline peak height. By adding trehalose and sucrose as an excipient the sodium chloride concentration decreased to a value of 9%. As a consequence, the crystalline peak no longer over-shadowed the amorphous halo caused by protein and stabilizer. As the mass ratio of sorbitol was lower than that of the disaccharides, the crystalline peak of sodium chloride could still be seen in the WAXD diagram of the sorbitol mixture.

Tonicity Calculations

As the afelimomab concentrate originally was developed and formulated for parenteral administration, isotonicity was an important factor. Reinhart et al., *Crit. Care Medicine* 29(4):765-769 (2001). Solutions for intravenous application should have about the same osmotic pressure as blood (286 mosmol/kg). Kommentar zum Europäischen Arzneibuch, Wiss. Verlagsgesellschaft Stuttgart mbH, Band 2 (5.2) (2006). The osmotic pressure can be calculated via freezing point depression using the following equations from Deutscher Arzneimittelcodex, dt. Apotheker Verlag Stuttgart, Band 1 (Anlage B), 1-6 (2006):

Calculation of the freezing point depression of 1% (w/V) solution:

$$\Delta T = \frac{L_{iso} \cdot 10}{M_r}$$

Calculation of ΔT of mixtures:

$$\Delta T_{mix} \Sigma \Delta T$$

Calculation of the osmotic pressure of a mixture:

$$\pi_{mix} = \frac{286\ mos\text{mol/kg} \cdot \Delta T_{mix}}{0.52°\text{ C.}}$$

In the above equations, ΔT represents the freezing point depression of a 1% (w/V) solution of the substance compared to pure water, $L_{iso}$ is the freezing point depression at isotonic concentration, and $M_r$ is the molecular weight. $L_{iso}$ values vary for different electrolytes (see Table 11). As the freezing point depression of serum is 0.52° C. (equaling an osmotic pressure of 286 mosmol/kg), the value for the freezing point depression of a 1% solution of the mixture compared to pure water ($\Delta T_{mix}$) should not exceed 0.52° C. The afelimomab with its high molecular weight did not have a substantial impact on the freezing point depression of the formulations, so it was not included in the calculations.

TABLE 11

| Substance | Liso | example |
|---|---|---|
| non-electrolyte | 1.9 | sucrose, trehalose, sorbitol |
| mono-monovalent electrolyte | 3.4 | NaCl |
| mono-trivalent electrolyte | 5.2 | Na3PO4 |

Using these equations the different concentrates and mixtures lead to the computed values of osmotic pressure given in Table 12.

TABLE 12

| Formulation | calc. osmotic pressure [mosmol/kg] |
|---|---|
| concentrate 12.4 mg/mL | 306 |
| concentrate 12.4 mg/mL + 25 mM sorb | 320 |
| concentrate 12.4 mg/mL + 25 mM treh | 332 |
| concentrate 12.4 mg/mL + 25 mM sucr | 332 |
| concentrate 50.6 mg/mL | 306 |
| concentrate 50.6 mg/mL + sorb | 361 |
| concentrate 50.6 mg/mL + treh | 412 |
| concentrate 50.6 mg/mL + sucr | 412 |
| concentrate 100 mg/mL | 307 |
| concentrate 100 mg/mL + sorb | 504 |
| concentrate 100 mg/mL + treh | 517 |
| concentrate 100 mg/mL + sucr | 517 |

To maintain physiological osmotic pressure, the amount of sodium chloride needed to be reduced when higher concentrated MAK 195F solutions were used. The original sodium chloride concentration was 8.8 mg/mL. Using the excipient: MAK 195F mass ratios estimated in this study (25 mM excipient in the concentrate 12.4 mg/mL), the protein concentration could be raised to about 130 mg/mL, provided that all sodium chloride was removed from the formulation. This resulted in an osmotic pressure of about 300 mosmol/kg.

Summary

This study demonstrates an exemplary method for preparing an antibody powder that includes spray drying. Specifically, in this example, an IgG fragment; afelimomab=MAK 195F solution was transformed into a dry bulk material. By screening various excipients and process conditions, a spray drying process was developed that provided process stability combined with storage stability.

Stability was analyzed by using various methods that can detect physical or chemical degradation of the protein, e.g., soluble and insoluble aggregation via SEC and DLS, thermal events via DSC, and humidity of the sd powders via Karl Fischer titration. Degradation took place during the drying process as caused by several stress factors, or was a result of long term storage at elevated temperature. The IgG fragment was stabilized by adding sugars to the protein. Trehalose, sucrose and sorbitol were studied for their stabilizing potential during drying and subsequent storage.

In the first part of the study, the protein concentrate was characterized and then spray dried without any excipients to check the susceptibility of the concentrate during the drying process. Furthermore a test series to find the right process parameters was conducted. Spray drying the pure concentrate lead to damage to the protein. The increase in aggregation was substantial (about 2%), particularly when subsequent storage was planned. Varying the $T_{In}$ should help to reduce aggregation, or to find the process parameters where least aggregation occurs.

Protein damage during the spray drying process seemed to be caused by the interplay of the different stress factors (e.g., heat, atomization, shear forces). None of these stress factors could solely cause deterioration of the protein comparable to the spray drying process.

The stabilizing sugars were added to the protein concentrate in various concentrations between 10 mM and 150 mM. 150 mM appeared to be unsuitable, since the solid content of the liquid feed was so high that the cyclone separator tended to clog, which resulted in a low powder yield. 10 mM addition of excipient was insufficient for all the tested sugars. The best results were obtained by addition of 25 mM, equaling a mass ratio of excipient:MAK 195F=0.7:1 for trehalose and sucrose and 0.35:1 for sorbitol. 50 mM lead to comparable results but the purpose was to minimize the amounts of additives to the extent possible. Comparing the stabilization potential for the spray drying process, trehalose and sucrose lead to similar results. Sorbitol appears to be a little inferior to the disaccharides. But this was not founded in the small mass ratio, where addition of more sorbitol did not improve the results. Concerning process stability, an addition of 25 mM of preferably trehalose or sucrose is recommended.

As the 25 mM mixtures were most effective for process stability, they were used for a short term stability tests (3 months). Together with analogous placebo mixtures and the liquid concentrate, the sd powders were exposed to 3 different commonly-used climates (fridge: 5° C., Central Europe: 25° C./60% RH, Southeast Asia: 45° C./75% RH). As expected, the liquid concentrate could not withstand any of the elevated temperatures, which resulted in severe protein damage after 1 month (aggregation, fragmentation and optical turbidity). The sd powders with excipients showed good stability over 3 months. Trehalose as well as sucrose formulations only suffered substantial damage when stored at 40° C./75% RH (aggregation increase of 2%). Even 25° C./60% RH had no impact on the powders except for a small increase in aggregation (0.5%). As the results for process stability implied, sorbitol was also the weakest stabilizer during storage. The mixtures stored at 5° C. and 25° C. were similarly stable with the other excipients, but 40° C. was a critical parameter for the sorbitol-protein mixture. 40° C. exceeded the Tg of the mixture, so storage stability caused by protein immobilization could no longer be guaranteed. This lead to an aggregation increase of about 12%, which had not been observed in any preliminary test of this study. Subvisible particle and turbidity measurements lead to unsatisfying results. These samples mostly showed visual turbidity or even coagulation. The main problem of the stability studies was the Al-vials used for storing the powders. They did not show complete water vapour impermeability, so the residual water content of the hygroscopic powders could not be kept constant.

With the judicious formulation, nearly all protein changes could be reduced to a minimum level. The only parameter still showing substantial change was turbidity. Not storage, but the spray drying process leads to an increase in turbidity. Attempts to lower this increase by addition of more excipient or the use of lower drying temperatures failed. An increase in turbidity from about 5 NTU (concentrate) to 15-20 NTU (sd mixtures) could not be avoided. Yet the other analytical methods did not show substantial changes during spray drying of the protein-sugar formulations.

In the last part of this study, the protein concentration in the liquid feed was increased with the goal of achieving a higher throughput of the spray dryer. Experiments with a protein concentration of 50.6 mg/mL were made. The process of ultrafiltration as well as spray drying the more concentrated protein solution (with the identified best mass ratio of sugar additive) did not have substantial impact on the stability of the afelimomab protein. Most results (except particle contamination or turbidity, according to the higher solid content) were comparable to the analogous experiments with the concentrate 12.4 mg/mL. Spray drying of concentrations of 100 mg/mL should be feasible if clogging of the cyclone exit can be prevented. Even the more concentrated powders could be administrated parenterally without running the risk of hypo- or hypertony, because the original buffer contains enough sodium chloride, which can be removed in exchange for the stabilizing agents. Protein concentrations of up to 130 mg/mL could be possible.

Composition of Antibody Formulations

Spray drying experiments were performed on a Büchi Mini-Spray Dryer B-191 as described previously. Briefly, the drying air was filtered through a Luwa Ultrafilter 2 (fiber glass; filterclass: HEPA H13) prior to entering the heating device and the drying chamber. All liquid feeds were filtered through a 0.22 µm filter unit before being transported to the drying chamber by a peristaltic pump (QLF=~3 mL/min; silicon tube Ø=3 mm). Atomization was performed by a two fluid nozzle using dry nitrogen ($Q_{AA}$=700 l/h). After spray drying the resulting powders were recovered from the collecting vessel and filled in glass vials (bromobutyl rubber stoppers), sealed with parafilm. The compositions are summarized in Table 13. Protein characterization was performed by using UV/VIS, SEC, IEC, PCS, DSC, XRD & Karl-Fischer method.

TABLE 13

|  | Sodium phosphate | Sodium chloride | Histidine | Trehalose | Pluronic F68 |
|---|---|---|---|---|---|
| MAK 195F 95 mg/mL | 1.64 mg/mL | 8.77 mg/mL | — | 65.58 mg/mL | 0.1 mg/mL |
| Adalimumab 100 mg/mL | — | — | 2.33 mg/mL | 69.03 mg/mL | 0.1 mg/mL |
| ABT-325 100 mg/mL | — | — | 2.33 mg/mL | 69.03 mg/mL | 0.1 mg/mL |

Figure 10A:
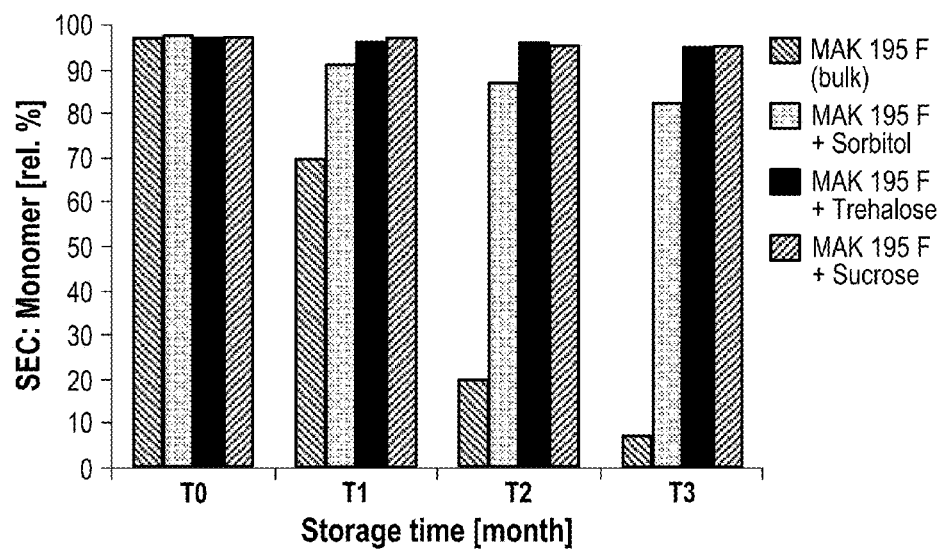
FIG. 10 depicts size exclusion chromatography (SEC) physical stability data for spray dried MAK 195F formulations: (A) effect of sorbitol, trehalose and sucrose and (B) effect of stabilizer concentration on the amount of protein aggregation.
Figure 10B:
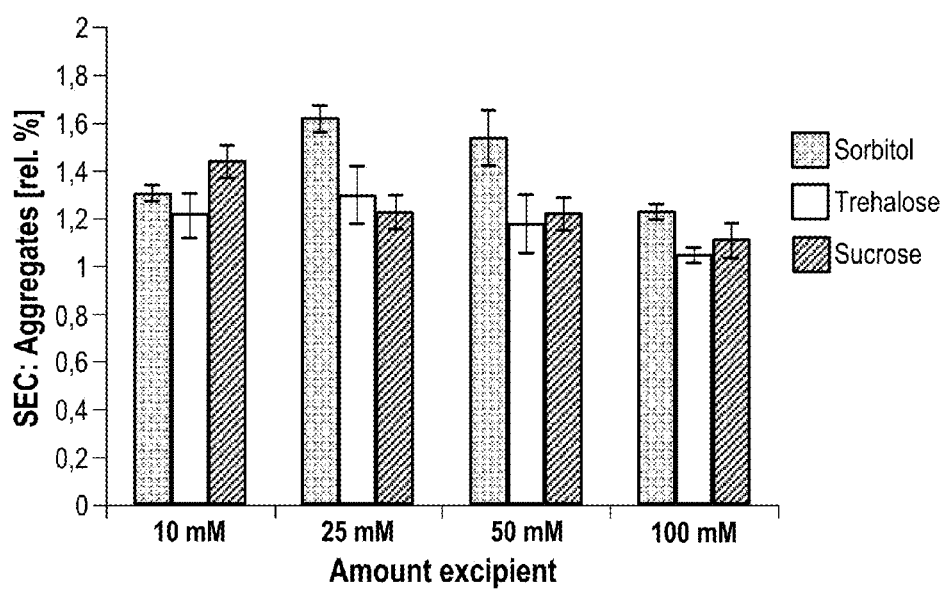

As discussed above, formulation and process parameters were evaluated using MAK 195 F as a model compound using a concentration of 12 mg/mL. FIG. 10 includes two bar graphs depicting SEC physical stability data for spray dried MAK 195F formulations: (A) effect of sorbitol, trehalose and sucrose (c=25 mM) and (B) effect of stabilizer concentration on the amount of protein aggregation after 3 months storage at 40° C./75% RH. The data given in FIG. 10A reveal that trehalose and sucrose provide the most stable products, while sorbitol did not provide adequate long term protein stability. The minimal amount of stabilizer was determined at 25 mM, equaling a mass ratio of excipient: protein=0.7:1 (see FIG. 10B). In FIG. 10A, the bars in each grouping, from left to right, represent MAK 195F (bulk), MAK 195F+sorbitol, MAK 195F+trehalose, and MAK 195F+sucrose, respectively. In FIG. 10B, the bars in each grouping, from left to right, represent sorbitol, trehalose, and sucrose, respectively.

Figure 11A:
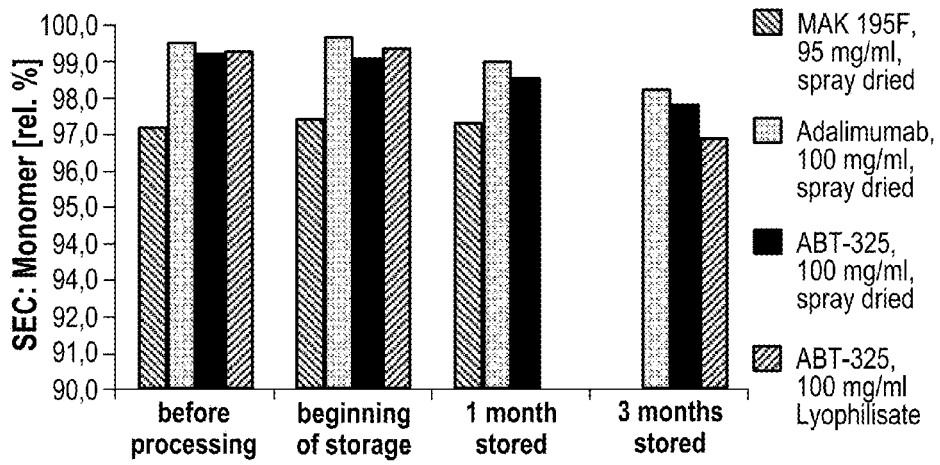
FIG. 11 depicts the effect of processing and 3 months storage (A) on physical stability and (B) on chemical stability for spray-dried high-concentration MAK 195F, Adalimumab, and ABT-325 in 200 mM trehalose solutions.

These parameters where reproduced by using protein concentrations ranging from 12, 50 and 100 mg/mL. All formulations provided acceptable powders. The average residual moisture shown in Table 14 was between 4.6 wt. % (MAK 195 F) and 5.5 wt. % (Adalimumab) and therefore considerably higher, compared to lyophilized formulations with typical values below 1%. Nevertheless, the glass transition temperatures were measured at 60° C. for MAK 195F and approximately 70° C. for both full antibodies, suggesting suitable stability at least at 5° C. storage temperature. Preliminary analytical data of these high concentration (100 mg/mL) spray dried MAK 195F, Adalimumab and ABT-325 formulations are presented in FIG. 11. FIG. 11 has two bar graphs depicting (A) the effect of processing and 3 months storage at 40° C./75% RH on physical stability by using SEC method, and (B) on chemical stability (standardized 100% after processing) determined by IEC method, for spray-dried high-concentration MAK 195F, Adalimumab, and ABT-325 in 200 mM trehalose solutions. In FIG. 11A the bars in each grouping, from left to right, represent MAK 195F (95 mg/mL, spray dried), adalimumab (100 mg/mL, spray dried); ABT-325 (100 mg/mL, spray dried); and ABT-325 (100 mg/mL, lyophilized), respectively (except there is no one month storage data for ABT-325 (100 mg/mL, lyophilized), and no 3 month storage data for MAK 195F (95 mg/mL, spray dried)).

TABLE 14

| Formulation | Residual Moisture [wt %] | Tg [° C.] |
|---|---|---|
| MAK 195F spray-dryed 95 mg/mL | 4.58 | 59.3 |
| Adalimumab spray-dryed 100 mg/mL | 5.46 | 70.4 |
| ABT-325 spray-dryed 100 mg/mL | 4.88 | 71.3 |

TABLE 14-continued

| Formulation | Residual Moisture [wt %] | Tg [° C.] |
|---|---|---|
| ABT-325 lyophilized 100 mg/mL | 0.29 | — |

Figure 11B:
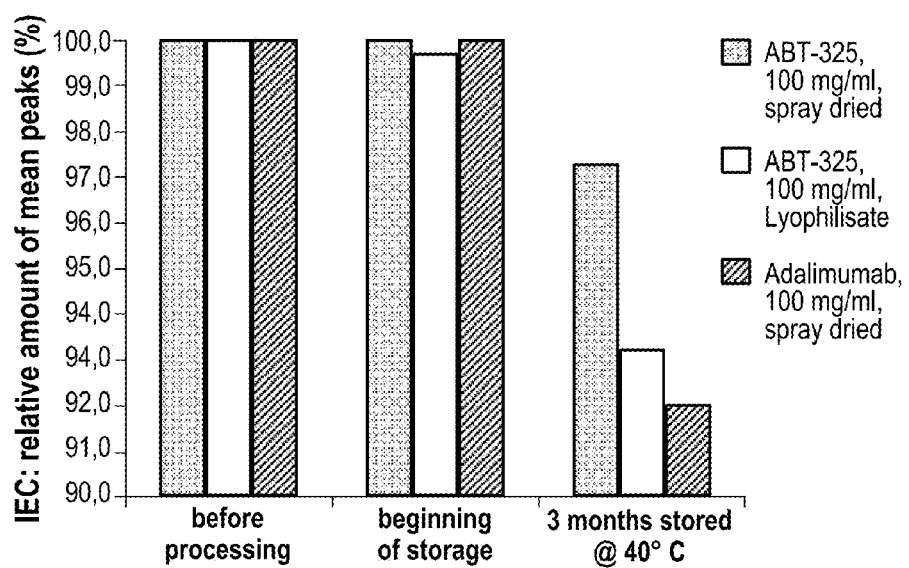

The data for all tested formulations demonstrate acceptable physical stability of the protein during processing and storage for up to three months at 40° C., equivalent to the ABT-325 lyophilizate. However, corresponding PCS-Data (not shown) suggest an effect on protein characteristics, which has to be analyzed in more detail. With regards to chemical stability, the data in FIG. 11B demonstrated comparable results for a spray dried formulation compared to a standard freeze-dried formulation. In FIG. 11B the bars in each grouping, from left to right, represent ABT-325 (100 mg/mL, spray dried), ABT-325 (100 mg/mL lyophilized), and adalimumab (100 mg/mL, spray dried), respectively.

Summary

This demonstrates the general feasibility of successfully manufacturing spray-dried antibody powders from mAb solutions with concentrations up to 100 mg/mL. The presented data for MAK 195F, Adalimumab and ABT-325 show neither a significant effect during processing nor during accelerated stability studies with regards to physical or chemical stability of the protein. However, observed polydispersion of spray-dried proteins should be analyzed in more detail.

Furthermore, a sufficient amount of stabilizer is required within the formulations to achieve long-term storage. Nevertheless, due to the versatility of this technique, it offers interesting prospects with regards to bulk drug substance formulation as well as towards new dosage forms and routes of administration.

INCORPORATION BY REFERENCE

The contents of all cited references (including literature references, patents, patent applications, and web sites) that may be cited throughout this application are hereby expressly incorporated by reference. The practice of the invention will employ, unless otherwise indicated, conventional techniques of spray drying and protein formulation, which are well known in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

The invention claimed is:

1. A pharmaceutical powder preparation comprising an effective amount of adalimumab and sodium hyaluronate,
wherein the pharmaceutical powder preparation is prepared by spray drying a solution comprising more than about 50 mg/mL of adalimumab and an excipient which is either trehalose or sucrose, and
wherein the pharmaceutical powder preparation has an excipient:adalimumab mass ratio of about 0.7:1.0 or about 1.4:1.0, comprises less than about 6% residual moisture, comprises no more than 2% aggregates upon reconstitution when stored as a powder at 25° C. for three months, and comprises no more than 5% aggregates upon reconstitution when stored as a powder at 40° C. for three months.

2. A pharmaceutical powder preparation comprising an effective amount of adalimumab,
wherein the pharmaceutical powder preparation is prepared by spray drying a solution comprising more than about 50 mg/mL of the adalimumab and an excipient which is either trehalose or sucrose, and
wherein the pharmaceutical powder preparation has an excipient:adalimumab mass ratio of about 0.7:1.0 or about 1.4:1.0, comprises less than about 6% residual moisture, comprises no more than 2% aggregates upon reconstitution when stored as a powder at 25° C. for three months, and comprises no more than 5% aggregates upon reconstitution when stored as a powder at 40° C. for three months.

3. A pharmaceutical powder preparation comprising an effective amount of a human anti-Tumor Necrosis factor alpha (TNFα) antibody and sodium hyaluronate,
wherein the pharmaceutical powder preparation is prepared by spray drying a solution comprising more than about 50 mg/mL of antibody and an excipient which is either trehalose or sucrose,
wherein the pharmaceutical powder preparation has an excipient:antibody mass ratio of about 0.7:1.0 or about 1.4:1.0, comprises less than about 6% residual moisture, comprises no more than 2% aggregates upon reconstitution when stored as a powder at 25° C. for three months, and comprises no more than 5% aggregates upon reconstitution when stored as a powder at 40° C. for three months, and
wherein the antibody comprises a light chain variable region (LCVR) having a CDR3 domain comprising the amino acid sequence of SEQ ID NO:3, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, a CDR2 domain comprising the amino acid sequence of SEQ ID NO: 6, and a CDR1 domain comprising the amino acid sequence of SEQ ID NO:8.

4. A pharmaceutical powder preparation comprising an effective amount of a human anti-Tumor Necrosis factor alpha (TNFα) antibody and sodium hyaluronate,
wherein the pharmaceutical powder preparation is prepared by spray drying a solution comprising more than about 50 mg/mL of the antibody and an excipient which is either trehalose or sucrose,
wherein the pharmaceutical powder preparation has an excipient:antibody mass ratio of about 0.7:1.0 or about 1.4:1.0, comprises less than about 6% residual moisture, comprises no more than 2% aggregates upon reconstitution when stored as a powder at 25° C. for three months, and comprises no more than 5% aggregates upon reconstitution when stored as a powder at 40° C. for three months, and
wherein the antibody comprises a light chain variable region (LCVR) having a CDR3 domain comprising the amino acid sequence of SEQ ID NO:3, a CDR2 domain comprising the amino acid sequence of SEQ ID NO:5, and a CDR1 domain comprising the amino acid sequence of SEQ ID NO: 7, comprises a heavy chain variable region (HCVR) having a CDR3 domain comprising the amino acid sequence of SEQ ID NO:4, a CDR2 domain comprising the amino acid sequence of SEQ ID NO: 6, and a CDR1 domain comprising the amino acid sequence of SEQ ID NO:8, and is an IgG.

5. A pharmaceutical powder preparation comprising an effective amount of a human anti-Tumor Necrosis factor alpha (TNFα) antibody and sodium hyaluronate,
wherein the pharmaceutical powder preparation is prepared by spray drying a solution comprising more than about 50 mg/mL of the antibody and an excipient which is either trehalose or sucrose,
wherein the pharmaceutical powder preparation has an excipient:antibody mass ratio of about 0.7:1.0 or about 1.4:1.0, comprises less than about 6% residual moisture, comprises no more than 2% aggregates upon reconstitution when stored as a powder at 25° C. for three months, and comprises no more than 5% aggregates upon reconstitution when stored as a powder at 40° C. for three months, and
wherein the antibody comprises an LCVR comprising the amino acid sequence set forth in SEQ ID NO: 1, and an HCVR comprising the amino acid sequence set forth in SEQ ID NO: 2.

6. The pharmaceutical powder preparation of claim 3, wherein the antibody comprises an LCVR comprising the amino acid sequence set forth in SEQ ID NO: 1, an HCVR comprising the amino acid sequence set forth in SEQ ID NO: 2, and is an IgG.

* * * * *

```
                         SEQUENCE LISTING

<160> NUMBER OF SEQ ID NOS: 8

<210> SEQ ID NO 1
<211> LENGTH: 107
<212> TYPE: PRT
<213> ORGANISM: Artificial Sequence
<220> FEATURE:
<223> OTHER INFORMATION: Variable light chain

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Gly Ile Arg Asn
                 20                  25                  30

Tyr Leu Ala Trp Tyr Gln Gln Lys Pro Gly Lys Ala Pro Lys Leu Leu
                 35                  40                  45

Ile Tyr Ala Ala Ser Thr Leu Gln Ser Gly Val Pro Ser Arg Phe Ser
                 50                  55                  60

Gly Ser Gly Ser Gly Thr Asp Phe Thr Leu Thr Ile Ser Ser Leu Gln
 65                  70                  75

Pro Glu Asp Val Ala Thr Tyr Tyr Cys Gln Arg Tyr Asn Arg Ala Pro
 80                  85                  90                  95

Tyr Thr Phe Gly Gln Gly Thr Lys Val Glu Ile Lys
                100                 105

<210> SEQ ID NO 2
<211> LENGTH: 121
<212> TYPE: PRT
<213> ORGANISM: Artificial Sequence
<220> FEATURE:
<223> OTHER INFORMATION: Variable heavy chain

<400> SEQUENCE: 2

Glu Val Gln Leu Val Glu Ser Gly Gly Gly Leu Val Gln Pro Gly
 1               5                  10                  15

Arg Ser Leu Arg Leu Ser Cys Ala Ala Ser Gly Phe Thr Phe Asp Asp
                 20                  25                  30

Tyr Ala Met His Trp Val Arg Gln Ala Pro Gly Lys Gly Leu Glu Trp
                 35                  40                  45

Val Ser Ala Ile Thr Trp Asn Ser Gly His Ile Asp Tyr Ala Asp Ser
                 50                  55                  60

Val Glu Gly Arg Phe Thr Ile Ser Arg Asp Asn Ala Lys Asn Ser Leu
 65                  70                  75
```

```
Tyr Leu Gln Met Asn Ser Leu Arg Ala Glu Asp Thr Ala Val Tyr Tyr
 80                  85                  90                  95

Cys Ala Lys Val Ser Tyr Leu Ser Thr Ala Ser Ser Leu Asp Tyr Trp
                100                 105                 110

Gly Gln Gly Thr Leu Val Thr Val Ser Ser
            115                 120

<210> SEQ ID NO 3
<211> LENGTH: 9
<212> TYPE: PRT
<213> ORGANISM: Artificial Sequence
<220> FEATURE:
<221> NAME/KEY: VARIANT
<222> LOCATION: 9
<223> OTHER INFORMATION: Xaa = Thr or Ala
<223> OTHER INFORMATION: Variable light chain CDR3

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<221> NAME/KEY: VARIANT
<222> LOCATION: 12
<223> OTHER INFORMATION: Xaa = Tyr or Asn
<223> OTHER INFORMATION: Variable heavy chain CDR3

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: Variable light chain CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: Variable heavy chain CDR2

<400> SEQUENCE: 6

Ala Ile Thr Trp Asn Ser Gly His Ile Asp Tyr Ala Asp Ser Val
 1               5                  10                  15

Glu Gly

<210> SEQ ID NO 7
<211> LENGTH: 11
<212> TYPE: PRT
<213> ORGANISM: Artificial Sequence
<220> FEATURE:
<223> OTHER INFORMATION: Variable light chain CDR1

<400> SEQUENCE: 7
```

-continued

```
Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: Variable heavy chain CDR1

<400> SEQUENCE: 8

Asp Tyr Ala Met His
 1               5
```